US010463348B2

(12) United States Patent
Shuart et al.

(10) Patent No.: US 10,463,348 B2
(45) Date of Patent: Nov. 5, 2019

(54) BIOPSY DEVICE WITH TIP PROTECTOR AND MOUNTING APPARATUS

(71) Applicant: Devicor Medical Products, Inc., Cincinnati, OH (US)

(72) Inventors: David Shuart, Mason, OH (US); Andrew Paul Nock, Dayton, OH (US); Andrew Robinson, Cincinnati, OH (US); Rachel Yoon Choung, Studio City, CA (US); Mark Graham, Maineville, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

(21) Appl. No.: 16/117,409

(22) Filed: Aug. 30, 2018

(65) Prior Publication Data

US 2019/0076133 A1   Mar. 14, 2019

Related U.S. Application Data

(63) Continuation of application No. 15/977,644, filed on May 11, 2018.

(Continued)

(51) Int. Cl.
*A61B 10/00* (2006.01)
*A61B 10/02* (2006.01)
(Continued)

(52) U.S. Cl.
CPC ...... *A61B 10/0233* (2013.01); *A61B 17/3403* (2013.01); *A61B 50/13* (2016.02);
(Continued)

(58) Field of Classification Search
CPC ............ A61B 2010/0208; A61B 10/02; A61B 10/0233; A61B 17/3403
(Continued)

(56) References Cited

U.S. PATENT DOCUMENTS

| 5,526,822 A | 6/1996 | Burbank et al. |
| 5,632,732 A * | 5/1997 | Szabo ................. A61M 5/3216 604/187 |

(Continued)

FOREIGN PATENT DOCUMENTS

| WO | WO 2004/084738 A1 | 10/2004 |
| WO | WO 2007/145926 A2 | 12/2007 |
| WO | WO 2015/110533 A2 | 7/2015 |

OTHER PUBLICATIONS

Hahn, Markus et al., "Vacuum Assisted Breast Biopsy with Mammotome®," available Nov. 11, 2012, copyright 2013 by Devicor Medical Germany GmbH, published in Germany by Springer Medizin Verlag. 128 pages.

(Continued)

*Primary Examiner* — Steven M Marsh
(74) *Attorney, Agent, or Firm* — Frost Brown Todd LLC

(57) ABSTRACT

A biopsy device holder includes a needle holder, a distal holder, and a proximal holder. The needle holder includes an elongated housing extending between an open proximal end and a distal end. The needle holder is adapted to releasably receive the biopsy device through the open proximal end. The elongated housing includes a coupler configured to couple the needle holder to the biopsy device. The distal holder includes an opening configured to pivotably receive the distal end of the needle holder. The proximal holder includes a longitudinal stop that engages with a portion of the needle holder to prevent the needle holder from proximal longitudinal movement. The longitudinal stop is configured to disengage the coupler of the needle holder from the biopsy device when the biopsy device is moved proximally in a longitudinal direction.

20 Claims, 21 Drawing Sheets

Related U.S. Application Data

(60) Provisional application No. 62/564,014, filed on Sep. 27, 2017, provisional application No. 62/505,660, filed on May 12, 2017.

(51) Int. Cl.
| | | |
|---|---|---|
| *A61B 50/13* | (2016.01) | |
| *A61B 90/57* | (2016.01) | |
| *A61B 17/34* | (2006.01) | |
| *A61B 90/11* | (2016.01) | |
| *A61B 50/20* | (2016.01) | |
| A61B 90/00 | (2016.01) | |
| A61B 50/15 | (2016.01) | |
| A61B 17/00 | (2006.01) | |
| A61B 50/00 | (2016.01) | |

(52) U.S. Cl.
CPC .............. *A61B 50/20* (2016.02); *A61B 90/11* (2016.02); *A61B 90/57* (2016.02); *A61B 2017/00477* (2013.01); *A61B 2017/3413* (2013.01); *A61B 2050/0082* (2016.02); *A61B 2050/155* (2016.02); *A61B 2090/0801* (2016.02)

(58) Field of Classification Search
USPC ............ 248/309.1, 309.2, 311.2, 311.3, 314; 604/204; 600/562
See application file for complete search history.

(56) References Cited

U.S. PATENT DOCUMENTS

| | | |
|---|---|---|
| 5,928,164 A | 7/1999 | Burbank et al. |
| 6,017,316 A | 1/2000 | Ritchart et al. |
| 6,086,544 A | 7/2000 | Hibner et al. |
| 6,162,187 A | 12/2000 | Buzzard et al. |
| 6,432,065 B1 | 8/2002 | Burdorff et al. |
| 6,626,849 B2 | 9/2003 | Huitema et al. |
| 6,752,768 B2 | 6/2004 | Burdorff et al. |
| 6,860,860 B2 | 3/2005 | Viola |
| 7,442,171 B2 | 10/2008 | Stephens et al. |
| 7,648,466 B2 | 1/2010 | Stephens et al. |
| 7,837,632 B2 | 11/2010 | Stephens et al. |
| 7,854,706 B2 | 12/2010 | Hibner |
| 7,914,464 B2 | 3/2011 | Burdorff et al. |
| 7,938,786 B2 | 5/2011 | Ritchie et al. |
| 8,083,687 B2 | 12/2011 | Parihar |
| 8,118,755 B2 | 2/2012 | Hibner et al. |
| 8,206,316 B2 | 6/2012 | Hibner et al. |
| 8,241,226 B2 | 8/2012 | Hibner et al. |
| 8,251,916 B2 | 8/2012 | Speeg et al. |
| 8,454,531 B2 | 6/2013 | Speeg et al. |
| 8,532,747 B2 | 9/2013 | Nock et al. |
| 8,622,924 B2 | 1/2014 | Speeg et al. |
| 8,702,623 B2 | 4/2014 | Parihar et al. |
| 8,764,680 B2 | 6/2014 | Rhad et al. |
| 8,801,742 B2 | 8/2014 | Rhad et al. |
| 8,858,465 B2 | 10/2014 | Fiebig |
| 8,938,285 B2 | 1/2015 | Fiebig et al. |
| 9,095,326 B2 | 8/2015 | Ritchie et al. |
| 9,326,755 B2 | 5/2016 | Fiebig et al. |
| 9,345,457 B2 | 5/2016 | Speeg et al. |
| 9,486,186 B2 | 11/2016 | Fiebig et al. |
| 2004/0054334 A1* | 3/2004 | Prais ................ A61B 17/205 604/263 |
| 2006/0074345 A1 | 4/2006 | Hibner |
| 2008/0214955 A1 | 9/2008 | Speeg et al. |
| 2009/0131821 A1 | 5/2009 | Speeg et al. |
| 2010/0152610 A1 | 6/2010 | Parihar et al. |
| 2010/0160819 A1 | 6/2010 | Parihar et al. |
| 2013/0144188 A1 | 6/2013 | Fiebig et al. |
| 2013/0218047 A1 | 8/2013 | Fiebig et al. |
| 2013/0310707 A1* | 11/2013 | Bakhtyari-Nejad-Esfahani .......... A61B 5/15003 600/576 |
| 2013/0324882 A1 | 12/2013 | Mescher et al. |
| 2014/0039343 A1 | 2/2014 | Mescher et al. |
| 2014/0275999 A1 | 9/2014 | Speeg et al. |
| 2016/0183928 A1 | 6/2016 | Speeg et al. |
| 2018/0185111 A1 | 7/2018 | Shuart et al. |
| 2018/0256819 A1* | 9/2018 | Shaw ................ A61M 5/24 |
| 2019/0060573 A1* | 2/2019 | Consolaro ............ A61M 5/288 |

OTHER PUBLICATIONS

U.S. Appl. No. 15/977,644, entitled "Biopsy Device with Tip Protector and Mounting Apparatus," filed May 11, 2018.
U.S. Appl. No. 15/829,499, entitled "Multi-Chamber Tissue Sample Cup for Biopsy Device," filed Dec. 1, 2017.
U.S. Appl. No. 15/829,483, entitled "Apparatus to Allow Biopsy Sample Visualization During Tissue Removal," filed Dec. 1, 2017.
U.S. Appl. No. 62/505,571, entitled "Biopsy Device with Sterile Sleeve," filed May 12, 2017.
U.S. Appl. No. 61/566,793, filed Dec. 5, 2011.
International Search Report and Written Opinion dated Nov. 2, 2018 for Application No. PCT/US2010/032336, 13 pgs.

* cited by examiner

BIOPSY DEVICE WITH TIP PROTECTOR AND MOUNTING APPARATUS

PRIORITY

This application claims priority to U.S. Provisional Patent App. No. 62/564,014 entitled "Biopsy Device with Tip Protector and Mounting Apparatus," filed Sep. 27, 2017, the disclosure of which is incorporated by reference herein.

This application also claims priority to U.S. Provisional Patent App. No. 62/505,660 entitled "Biopsy Device with Quick Release Tip Protector," filed May 12, 2017, the disclosure of which is incorporated by reference herein.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample may be analyzed at a lab (e.g. a pathology lab, biomedical lab, etc.) that is set up to perform the appropriate tests (such as histological).

Biopsy samples have been obtained in a variety of ways in various medical procedures including open and percutaneous methods using a variety of devices. For instance, some biopsy devices may be fully operable by an operator using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

The state of the art for breast biopsy is vacuum-assisted breast biopsy. A current textbook in this area is "Vacuum-Assisted Breast Biopsy with Mammotome®," available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

Biopsy devices may be used under ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used. The following briefly describes ultrasound image guided biopsy procedures, stereotactic guided biopsy procedures and MRI guided biopsy procedures.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454,531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015; U.S. Pat. No. 9,095,326, entitled "Biopsy System with Vacuum Control Module," issued Aug. 4, 2015 and U.S. Pat. No. 9,326,755, entitled "Biopsy Device Tissue Sample Holder with Bulk Chamber and Pathology Chamber," issued May 3, 2016. The disclosure of each of the above-cited U.S. patents is incorporated by reference herein.

Additional merely exemplary biopsy devices and biopsy system components are disclosed in U.S. Pub. No. 2006/0074345, entitled "Biopsy Apparatus and Method," published Apr. 6, 2006 and now abandoned; U.S. Pub. No. 2008/0214955, entitled "Presentation of Biopsy Sample by Biopsy Device," published Sep. 4, 2008; U.S. Patent Pub. No. 2009/0131821, entitled "Graphical User Interface For Biopsy System Control Module," published May 21, 2009, now abandoned; U.S. Pub. No. 2010/0152610, entitled "Hand Actuated Tetherless Biopsy Device with Pistol Grip," published Jun. 17, 2010, now abandoned; U.S. Pub. No. 2010/0160819, entitled "Biopsy Device with Central Thumbwheel," published Jun. 24, 2010, now abandoned; U.S. Pub. No. 2013/0144188, entitled "Biopsy Device With Slide-In Probe," published Jun. 6, 2013, issued as U.S. Pat. No. 9,486,186 on Nov. 8, 2016; and U.S. Pub. No. 2013/

0324882, entitled "Control for Biopsy Device," published Dec. 5, 2013, abandoned on Apr. 27, 2016. The disclosure of each of the above-cited U.S. patent application Publications is incorporated by reference herein.

U.S. Pub. No. 2014/0275999, entitled "Biopsy device" published Sep. 18, 2014, and U.S. Pub. No. 2016/0183928, entitled "Biopsy Device," published Jun. 30, 2016, both describe some aspect of a biopsy device including a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

While several systems and methods have been made and used for obtaining and processing a biopsy sample, it is believed that no one prior to the inventor has made or used the invention described in the appended claims.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
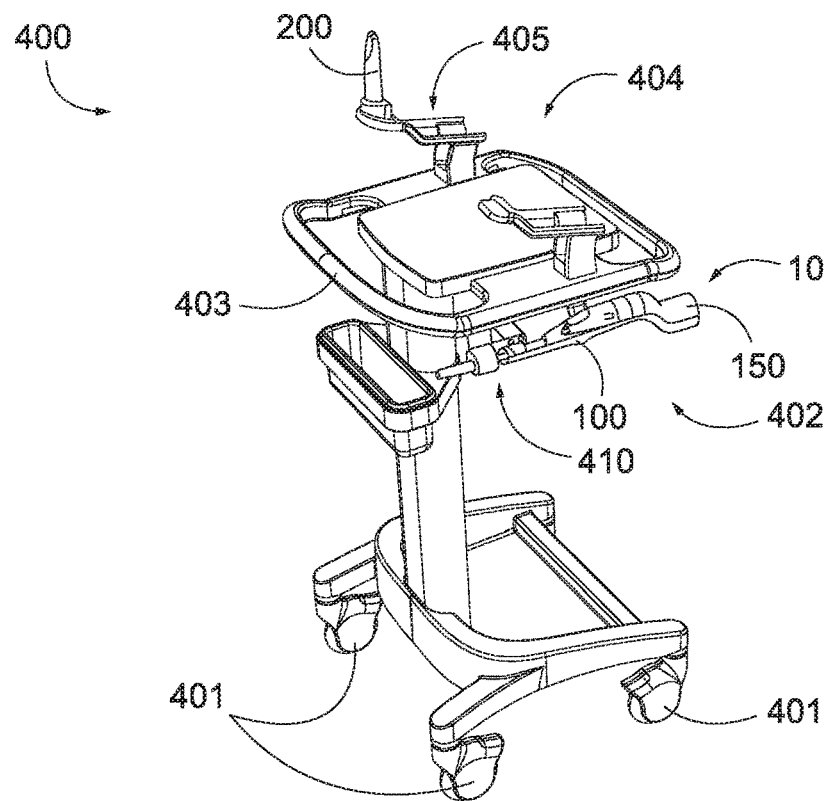
FIG. 1 depicts a perspective view of an exemplary control module cart including an exemplary device holder, with the device holder holding a biopsy device coupled to an exemplary probe protector.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Exemplary Control Module Cart

Figure 2:
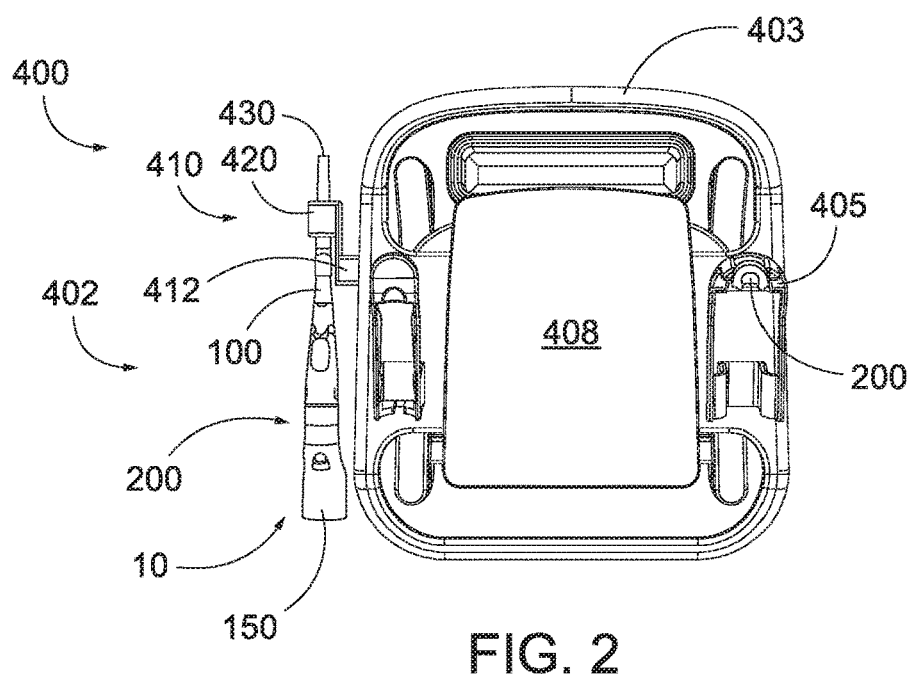
FIG. 2 depicts a top plan view of the control module cart of FIG. 1.

FIG. 1 shows an exemplary control module cart (400) to be used by an operator in various medical procedures. Control module cart (400) provides an operator with an easily accessible apparatus to store and retrieve various tools, devices, supplies, instruments, etc. during a medical procedure. As merely an illustrative example, control module cart (400) can include a stereotactic holder, an ultrasound holder, and other features. Control module cart (400) includes a transportability feature (401), a handle (403) and a cart surface (408). Transportability feature (401) is configured to allow control module cart (400) to be selectively transported such that an operator may move control module cart (400) to a desired position in a procedure room during a medical procedure. In the present example, transportability feature (401) are wheels positioned along a bottom side of control module cart (400). Handle (403) is configured to be selectively maneuvered to thereby navigate control module cart (400) to the desired position. As best seen in FIG. 2, cart surface (408) is configured to provide a plane surface on control module cart (400) wherein an operator may utilize as desired during the medical procedure. Control module cart (400) further includes, among other features, a holster holder (405) and a device holder (410). Holster holder (405) extends towards a top side (404) of control module cart (400), away from cart surface (408). Device holder (410) extends outwardly from a left side (402) of control module cart (400).

As best seen in FIG. 2, device holder (410) comprises an extension (412) and a mount (420). Extension (412) is fixedly attached to control module cart (400) on a first end and extends laterally from the side (402) of control module cart (400). Mount (420) is fixedly attached to extension (412) on a second end, away from control module cart (400). As will be described in greater detail below, mount (420) is generally configured to releasably receive a probe protector (430) to thereby hold probe protector (430) in physical isolation from cart surfaces (408) and other plane surfaces in the procedure room.

II. Exemplary Biopsy Device

Figure 3A:
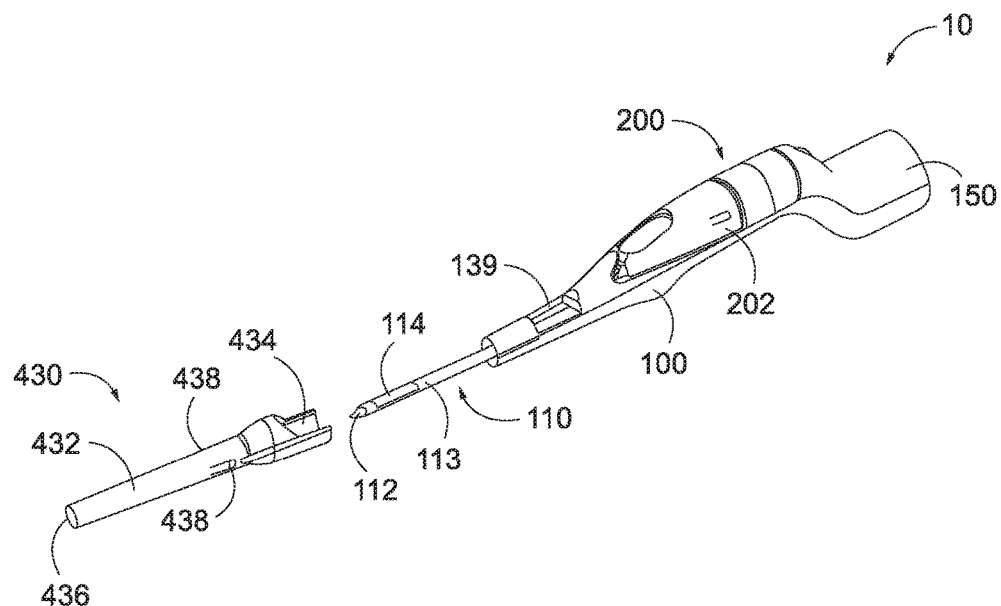
FIG. 3A depicts a perspective view of the probe protector of FIG. 1 decoupled from the biopsy device.
Figure 3B:
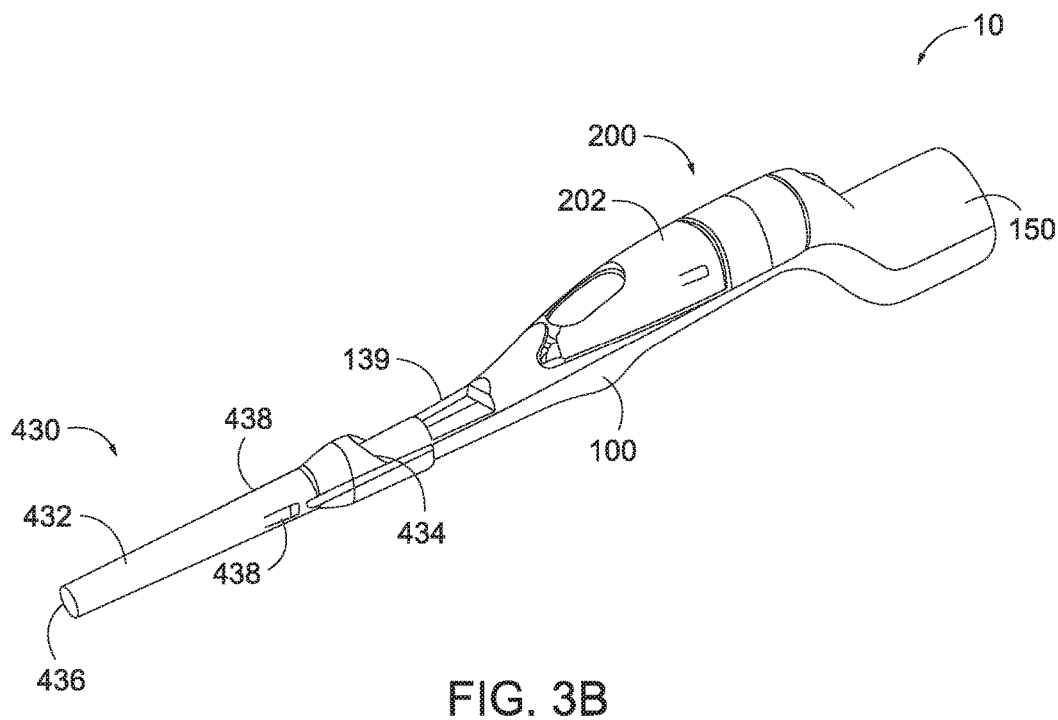
FIG. 3B depicts a perspective view of the probe protector of FIG. 1 coupled to the biopsy device.

As seen in FIG. 3A-3B, biopsy device (10) of the present examples includes a probe (100) and a holster (200). A needle (110) extends distally from probe (100) and is inserted into a patient's tissue to obtain tissue samples that are thereby deposited in a tissue sample holder (150) at the proximal end of probe (100). Holster (200) of the present example is selectively attachable to probe (100) to provide actuation of various components within probe (100). In the present configuration, holster (200) is a reusable component, while probe (100) and tissue sample holder (150) are disposable. It should be understood that the use of the term "holster" herein should not be read as requiring any portion of probe (100) to be inserted into any portion of holster (200). For instance, in the present example, holster (200) may include a retention feature (not shown) that is received by probe (100) to releasably secure probe (100) to holster (200).

Probe (100) also includes a set of resilient tabs (not shown) or other suitable release features that may be pressed inwardly to disengage retention feature (not shown), such that an operator may simultaneously depress both of the tabs then pull probe (100) rearwardly and away from holster (200) to decouple probe (100) from holster (200). Alternatively, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a Hall effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Alternatively, such sensors and features may be varied or omitted as desired.

Biopsy device (10) of the present example is configured for handheld use and be used under ultrasonic guidance. Alternatively, biopsy device (10) may instead be used under stereotactic guidance, MRI guidance, PEM guidance, BSGI guidance, or otherwise. It should also be understood that biopsy device (10) may be sized and configured such that biopsy device (10) may be operated by a single hand of an operator. In particular, an operator may grasp biopsy device (10), insert needle (110) into a patient's breast, and collect one or a plurality of tissue samples from within the patient's breast, all with just using a single hand. Such tissue samples may be deposited in tissue sample holder (150), and later retrieved from tissue sample holder (150) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein. Alternatively, an operator may grasp biopsy device (10) with more than one hand and/or with any desired assistance. In still other examples, biopsy device (10) can be configured to be secured to a table or other fixture without handheld operation.

In some settings, whether biopsy device (10) is handheld or mounted to a fixture, the operator may capture a plurality of tissue samples with just a single insertion of needle (110) into the patient's breast. Such tissue samples may be deposited in tissue sample holder (150), and later retrieved from tissue sample holder (150) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

Holster (200) of the present example includes an outer housing (202) that is configured to at least partially encompass the internal components of holster (200). Although not shown, it should be understood that holster (200) of the present example includes one or more motors and/or other actuators that are configured to drive various components of probe. To communicate power or movement to probe (100), holster (200) can include one or more gears. For instance, in some examples, one or more gears at least partially extend through an opening in outer housing (202). The opening in outer housing (202) can be configured to align with a corresponding opening associated with probe (100) to thereby permit the one or more gears of holster (200) to mesh with one or more corresponding gears of probe (100).

Although not shown, it should be understood that holster (200) may also include various cables that are configured to couple holster (200) to a control module or another control feature. Suitable cables may include electrical cables, rotary drive cables, pneumatic cables, or some combination thereof. Accordingly, it should be understood that in some examples, internal components within holster (200) may be powered by electrical power (electrical cables), rotary power (rotary drive cable), and/or pneumatic power (pneumatic cables). Alternatively, in some examples the cables are omitted entirely and holster (200) can be battery powered with motors and vacuum pumps being entirely contained within holster (200).

Holster (200) of the present example is configured as a reusable portion, while probe (100) is configured as a disposable portion. In some contexts, it may be desirable to maintain sterility of reusable components during a biopsy procedure. Accordingly, in some instances it may be desirable to use holster (200) in connection with certain shielding features to maintain the sterility of holster (200), while also maintaining functionality of holster (200). By way of example, a removable cover assembly configured to removably couple to holster (200) may be constructed and operable to provide sterility protection to the various components of holster (200). The removable cover assembly may include a set of sleeves configured to engage and encase holster (200) without interfering with the functionality of holster (200) or the attachment features that provide for the engagement of holster (200) to probe (100). Suitable shielding features and/or removable cover assemblies may be constructed in accordance with at least some of the teachings disclosed in U.S. App. No. 62/505,571 entitled "Biopsy Device with Sterile Sleeve," filed on May 12, 2017, the disclosure of which is incorporated by reference herein.

As described above with respect to holster (200), probe (100) is selectively couplable to holster (200) so that holster (200) may provide power or otherwise actuate probe (100). In some examples, holster (200) includes a locating feature (not shown) at the distal end of holster (200). Holster (200) further includes a retention feature (not shown) at the proximal end of holster (200). Locating feature is sized and configured to securely fit holster (200) into a corresponding receiving feature of probe (100) when holster (200) is attached to probe (100) along outer housing (not shown). Retention feature is sized and configured to securely attach holster (200) onto probe (100) by latching against a catch (not shown) of probe (100). Catch includes an aperture at the proximal end of probe (100) configured to receive retention feature. Latch (not shown) of probe (100) is positioned proximally to catch and is in mechanical communication with catch to thereby be operable to disengage catch from retention feature of holster (200).

Upon actuating latch and disengaging catch from retention feature, holster (200) becomes decoupled from outer housing of probe (100). Alternatively, a variety of other types of structures, components, features, etc. (e.g., bayonet mounts, clamps, clips, snap fittings, etc.) may be used to provide removable coupling of probe (100) and holster (200). While only a few exemplary attachment configurations have been described for holster (200), other various configurations may be provided as will be apparent to those of ordinary skill in the art in view of the teachings herein. Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein. By way of example, holster (200) may be configured and operable to be encased within a removable cover assembly prior to coupling with probe (100) as described in U.S. App. No. 62/505,571 entitled "Biopsy Device with Sterile Sleeve," filed on May 12, 2017, the disclosure of which is incorporated by reference herein.

Probe (100) of the present example further includes a needle (110) extending distally from probe (100) that is inserted into a patient's tissue to obtain tissue samples. These tissue samples are deposited in a tissue sample holder (150) at the proximal end of probe (100). In some examples, a vacuum control module (not shown) is coupled with probe (100) via a valve assembly (not shown) and tubes (not shown), which is operable to selectively provide vacuum, saline, atmospheric air, and venting to probe (100). By way of example only, the internal components of the valve assembly may be configured and arranged as described in U.S. Pat. Pub. No. 2013/0218047, entitled "Biopsy Device Valve Assembly," published Aug. 22, 2013, the disclosure of which is incorporated by reference herein.

Needle (110) of the present example comprises a cannula (113) having a piercing tip (112), and a lateral aperture (114) located proximal to tip (112), as best seen in FIG. 3A. Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," filed Jun. 1, 2011, the disclosure of which is incorporated by reference herein. As another merely illustrative example, tip (112) may be configured in accordance with at least some of the teachings in U.S. Pat. No. 9,486,186, entitled "Biopsy Device with Slide-In Probe," issued Nov. 8, 2016, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (not shown) having a sharp distal edge (not shown) is located within needle (110). Cutter is operable to rotate and translate relative to needle (110) and past lateral aperture (114) to sever a tissue sample from tissue protruding through lateral aperture (114). For instance, cutter may be moved from an extended position to a retracted position, thereby "opening" lateral aperture (114) to allow tissue to protrude therethrough; then from the retracted position back to the extended position to sever the protruding tissue.

In some examples, it may be desirable to rotate needle (110) to orient lateral aperture (114) at a plurality of desired angular positions about the longitudinal axis of needle (110). In the present example, needle (110) can be rotated by a motor disposed in probe (100) or holster (200). In other examples, needle (110) is manually rotatable by a thumbwheel on probe (100) or needle hub directly overmolded onto needle (110). Regardless, it should also be understood that, as with other components described herein, needle (110) may be varied, modified, substituted, or supplemented in a variety of ways; and that needle (110) may have a variety of alternative features, components, configurations, and functionalities. For instance, needle (110) may be constructed and operable in accordance with at least some of the teachings of U.S. Pat. No. 9,345,457, issued May 24, 2016, the disclosure of which is incorporated by reference herein; and/or in accordance with the teachings of any other reference cited herein.

Tissue sample holder (150) is selectively couplable to the proximal end of probe (100). In some examples, tissue sample holder (150) may be configured to operate in two discrete sample collection modes—a bulk tissue collection mode and an individual tissue collection moved. By way of example only, tissue sample holder (150) may be constructed and operable in accordance with at least some of the teachings of U.S. application Ser. No. 15/829,499, entitled "Multi-Chamber Tissue Sample Cup for Biopsy Device," filed on Dec. 1, 2017, the disclosure of which is incorporated by reference herein. By way of further example, tissue sample holder (150) may be constructed and operable in accordance with at least some of the teachings of any of the other references cited herein; and/or in any other suitable fashion.

The distal portion of probe (100) further includes a tissue sample window (139) disposed proximally of the distal end of probe (100). In some examples, tissue sample window (139) exposes a gate assembly (not shown), such that the gate assembly is visible to an operator though probe (100). The gate assembly is generally configured to selectively arrest movement of the severed tissue sample within the fluid conduit between the cutter and the tissue sample holder (150). The gate assembly is enables the operator to temporarily cease progression of tissue samples for visual inspection though a sample window (139) of probe (100). At least a portion of the gate assembly is coupled to cutter to communicate rotational and translational motion of gate assembly to cutter. Thus, it should be understood that rotation and translation of cutter drive member (not shown) results in corresponding rotation and translation of cutter via the coupling between at least a portion of the gate portion and at least a portion of the gate assembly. In some examples, the gate assembly may be constructed in accordance with the teachings of U.S. application Ser. No. 15/829, 483, entitled "Apparatus to Allow Biopsy Sample Visualization During Tissue Removal," filed on Dec. 1, 2017, the disclosure of which is incorporated by reference herein. Alternatively, probe (100) may simply lack a gate assembly, such that severed tissue samples are allowed to travel freely to tissue sample holder (150).

III. Exemplary Sterile Probe Protector And Device Holder

In some instances, it may be beneficial for biopsy device (10) to be temporarily stationed in a sterile holding location capable of maintaining the sterility of the sterile surfaces of biopsy device (10) while also being easily accessible by an operator for immediate use in a biopsy procedure. As is common during a biopsy procedure, an operator must be cautious to maintain the sterility of his/her hands and any tools, instruments or devices that are to ultimately contact the patient's body during the medical procedure. As such, being aware of the state of cleanliness of the procedure room's surroundings and identifying any non-sterile surfaces to avoid contact with is a critical practice employed in almost all medical procedures. In biopsy devices such as biopsy device (10) described above, it may be beneficial to provide certain assemblies or measures to maintain the sterility of the other components of biopsy device (10). However, it may not be feasible to incorporate a protective barrier or sleeve over the entire exterior of biopsy device (10), such as the removable cover assembly referenced above. Alternatively, it may be desirable to provide an additional measure of sterility in combination with the removable cover assembly referenced above.

Providing a device holder that is configured suspend biopsy device (10) in air and away from plane surfaces that have the potential to comprise the sterility of probe (100), needle (110), tissue sample holder (150), or other component of biopsy device (10), may be beneficial during various medical procedures, including but not limited to biopsy procedures. Incorporating a mechanism that allows for the quick release of biopsy device (10) with the use of one hand may also be desirable to further promote the ease in implementing the sterility measure created by the device holder. Furthermore, it may be desirable to include the device holder on an instrument commonly used during medical procedures to thereby increase the convenience for an operator in utilizing the device holder and maintaining the sterility of biopsy device (10), such as control module cart (400) described above. A separate holster holder that is configured to suspend holster (200) in air and away from plane surfaces that have the potential to comprise the sterility of holster (200) may also be beneficial during various medical procedures. Incorporating a mechanism that allows for holster (200) to be in a mounted position may be desirable to further promote the sterility of holster (200).

The following description provides various examples of a biopsy device holder and corresponding quick release mechanism that are cooperatively configured to maintain the sterility of the biopsy device while providing easy accessibility of the device for an operator. Ultimately, maintaining the biopsy device in a holder may be beneficial to ensure the surgical instrument is not contacting a non-sterile surface at any point during a medical procedure. It should be understood that the device holder features described below may be readily incorporated with any suitable variation of biopsy device (10) described above and in any of the various surgical procedures described in the various references described above. Other suitable ways in which the below-described device holder and sterile probe protector may be used will be apparent to those of ordinary skill in the art in view of the teachings herein.

A. Probe Protector with Resilient Latches

As previously indicated, control module cart (400) includes, among other features and instrument holders, device holder (410) including extension (412), mount (420), and a probe protector (430). As seen in FIG. 2, mount (420) is fixedly attached to extension (412) away from control module cart (400) and is suspended in air such that mount (420) is not in contact with any cart surfaces (408) or other plane surface (not shown) in the procedure room. Probe protector (430) is an elongated housing configured to be releasably received within mount (420) such that mount (420) may hold probe protector (430) in physical isolation from extension (412), cart surfaces (408), and other plane surfaces in the procedure room. Probe protector (430) is formed of a hard-plastic material to prevent fluid communication in and out of probe protector (430) when probe protector (430) is coupled to biopsy device (10).

As seen in FIGS. 3A-3B, probe protector (430) includes a closed distal end (436) and an open proximal end (434) separated by a hollow elongated shaft (432). As will be understood, probe protector (430) is generally configured to cover needle (110) of biopsy device (10) to thereby prevent inadvertent contact with piercing tip (112) of needle (110). Open proximal end (434) is sized and shaped to slidably receive and securely hold biopsy device (10) within elongate shaft (432). As shown in FIG. 3B, needle (110) may be inserted into open proximal end (434) and slidably translated through elongate shaft (432) until probe (100) becomes firmly secured within probe protector (430). Elongate shaft (432) includes a longitudinal length greater than the longitudinal length of needle (110) such that needle (110) is completely covered when inserted into probe protector (430). Piercing tip (112) and cannula (113) of needle (110) are shielded from coming into contact with mount (420), cart surface (408) or any other contacting surfaces (not shown) when biopsy device (10) is inserted into probe protector (430) due to closed distal end (436).

As further seen in FIGS. 3A-3B, probe protector (430) includes a pair of resilient latches (438) and locking tabs (439) positioned proximally along an exterior surface of elongate shaft (432). As will be described in greater detail below, resilient latches (438) and locking tabs (439) are generally configured to engage at least a portion of mount (420) to selectively secure probe protector (430) to mount (420). Resilient latches (438) and locking tabs (439) protrude outward from elongate shaft (432) and are configured to releasably attach probe protector (430) to mount (420). Although resilient latches (438) and locking tabs (439) of the present example are shown as being integral to the exterior surface of elongate shaft (432), it should be understood that in other examples resilient latches (438) and locking tabs (439) are configured as separate components. In addition, or in the alternative, it should be understood that resilient latches (438) and locking tabs (439) may include numerous alternative geometric configurations in other examples. Alternatively, other suitable alternative configurations for resilient latches (438) and locking tabs (439) will be apparent to those of ordinary skill in the art in view of the teachings herein. By way of example only, resilient latches (438) may take the form of springs tabs that are configured to flexibly deflect in multiple directions.

Figure 4A:
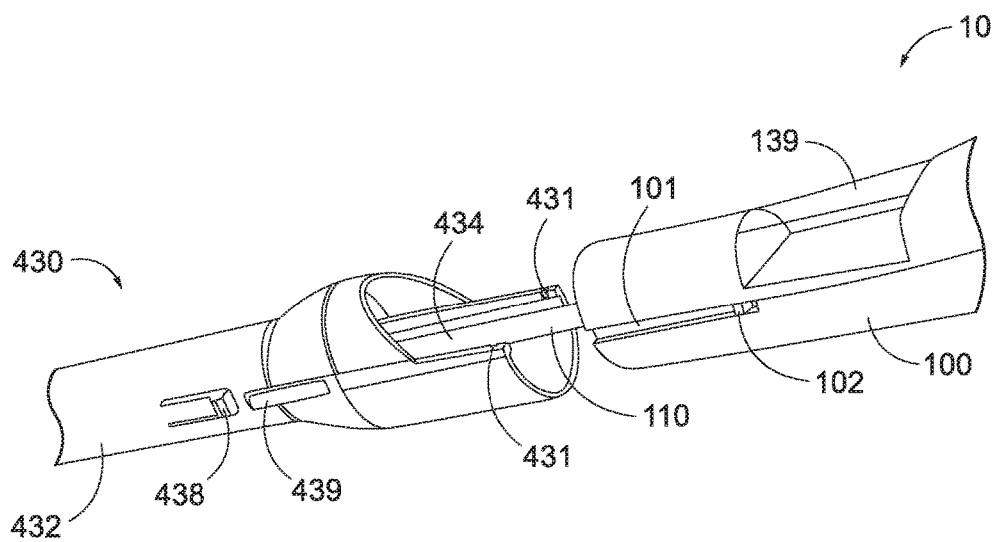
FIG. 4A depicts a partial perspective view of the probe protector of FIG. 1 decoupled from the biopsy device.
Figure 4B:
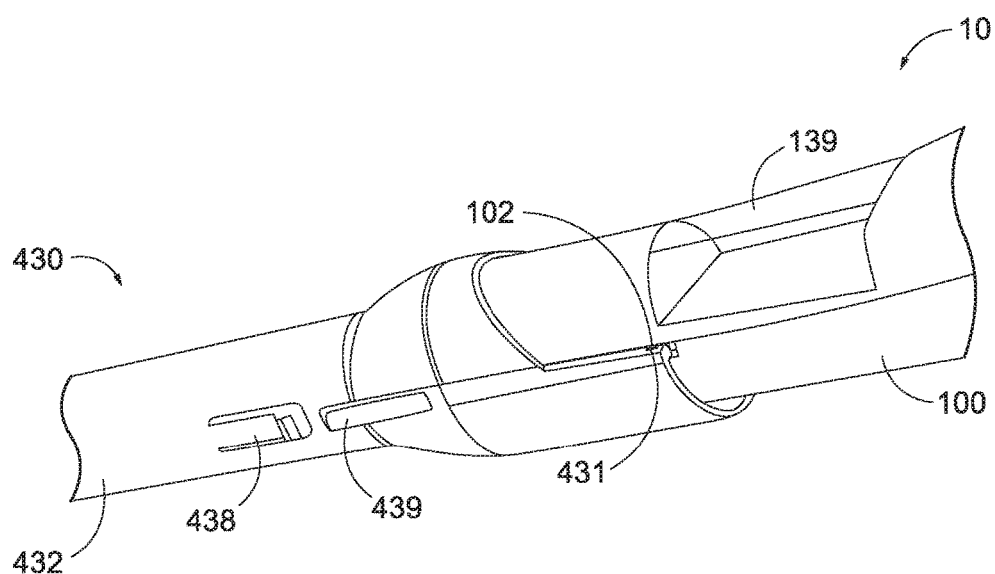
FIG. 4B depicts a partial perspective view of the probe protector of FIG. 1 coupled to the biopsy device

As best seen in FIG. 4A, probe protector (430) further includes a pair of notches (431) adjacent to open proximal end (434). Probe (100) includes a track (101) and a pair of prongs (102) positioned between tissue sample window (139) and needle (110). Track (101) is configured to receive and guide notches (431) of probe protector (430) towards prongs (102). As best seen in FIG. 4B, prongs (102) are configured to releasably secure biopsy device (10) to probe protector (430) by engaging notches (431) of probe protector (430). In the present example, notches (431) are sized and shaped to receive prongs (102) to thereby securely engage probe protector (430) to probe (100). Prongs (102) and notches (431) include corresponding chamfered surfaces such that prongs (102) and notches (431) are cooperatively configured to disengage each other upon the application of a predetermined opening force. In this instance, urging probe protector (430) in the distal direction relative to probe (100) and/or urging probe (100) in the proximal direction relative to probe protector (430) effectively separates probe protector (430) and probe (100) from the engaged position shown in FIG. 4B.

Figure 5:
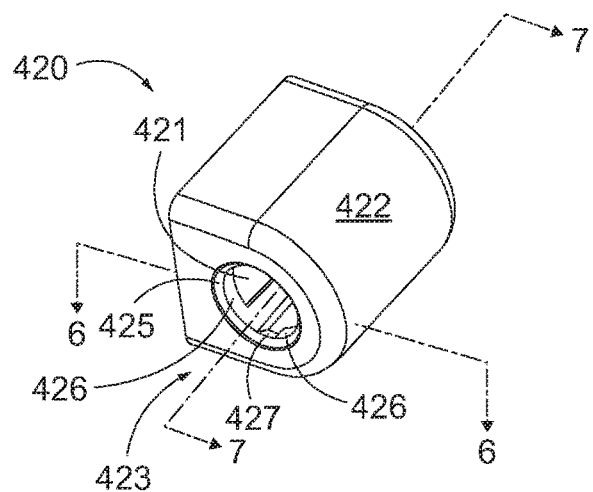
FIG. 5 depicts a perspective view of the device holder of FIG. 1.

As best seen in FIG. 5, mount (420) includes a receiving channel (421) positioned within an exterior housing (422) and extending between a front-end opening (423) and a rear-end opening (424). Front-end opening (423) includes a chamfered edge (425), an inner shelf (426) and a pair of ramps (427). Front-end opening (423) is configured to receive probe protector (430) and thereby direct closed distal end (436) and elongate shaft (432) through receiving channel (421) and out from rear-end opening (423).

Figure 6:
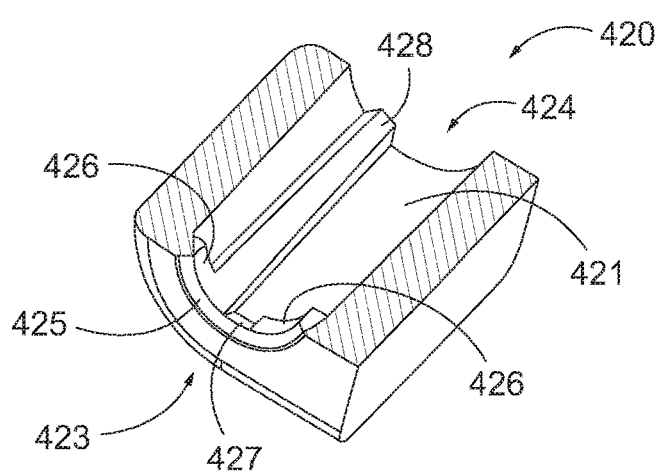
FIG. 6 depicts a perspective cross-sectional view of the device holder of FIG. 1, with the cross-section taken along line 6-6 of FIG. 5.

FIG. 6 shows chamfered edge (425) positioned along the perimeter of front-end opening (423). Chamfered edge (425) is configured to direct resilient latches (438) inward towards receiving channel (421) when probe protector (430) is inserted into mount (420). In particular, resilient latches (438) are configured to bend inwardly into elongate shaft (432) when a lateral force is exerted upon the protrusions of resilient latches (438), such as the lateral force created by chamfered edge (425) when resilient latches (438) are pressed against chamfered edge (425) as probe protector (430) is slidably inserted into mount (420). Resilient latches (438) may be inserted into receiving channel (421) at any rotational angle as chamfered edge (425) is uniformly positioned along the whole perimeter of front-end opening (423). Locking tabs (439) are configured to prevent probe protector (430) from slidably translating further into receiving channel (421) beyond the position of locking tabs (439). Although chamfered edge (425) is shown and described herein as being chamfered, it should be understood that in other examples chamfered edge (425) includes a variety of other configurations. For instance, in some examples chamfered edge (425) includes a concavely or convexly rounded surface to manipulate resilient latches (438) as described above.

Adjacent to chamfered edge (425), inner shelf (426) is positioned proximal to front-end opening (423). In the present example, inner shelf (426) extends uniformly along the whole perimeter of front-end opening (423). Inner shelf (426) includes a flat surface oriented laterally relative to an axis defined between openings (423, 424). This flat surface defined by inner shelf (426) is generally configured to inhibit resilient latches (438) from being withdrawn from receiving channel (421) of mount (420) by creating a physical barrier extending into receiving channel (421) that is configured to catch against resilient latches (438). Thus, inner shelf (426) serves to securely hold probe protector (430) within mount (420) by inhibiting the slidable translation of resilient latches (438) out from receiving channel (421).

Mount (420) further includes a pair of inner walls (428) contained in channel (421). Inner walls (428) extend longitudinally through channel (421) such that inner walls (428) extend between rear-end opening (424) and inner shelf (426). Inner walls (428) include a height extending internally into channel (421) substantially similar to a height of inner shelf (426). Inner walls (428) extend from inner shelf (426) at a position adjacent to ramps (427) such that inner walls (428) are configured to direct resilient latches (438) of probe protector (430) towards ramps (427).

Figure 7:
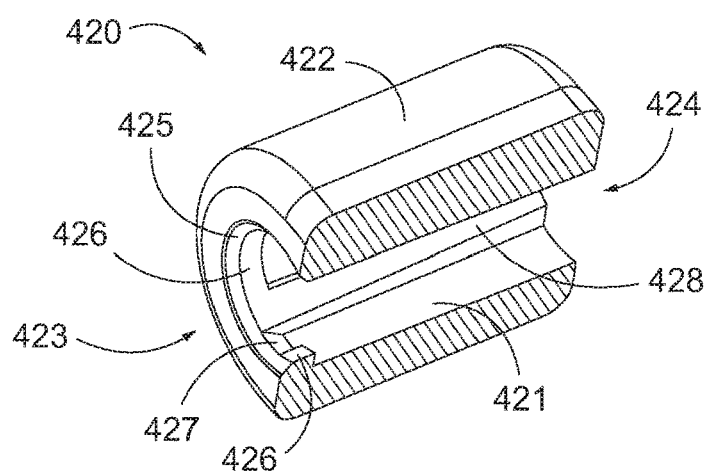
FIG. 7 depicts a perspective cross-sectional view of the device holder of FIG. 1, with the cross-section taken along line 7-7 of FIG. 5.

As seen in FIGS. 6-7, inner walls (428) extend along the longitudinal length of receiving channel (421) and are positioned adjacent the pair of ramps (427). By rotating probe protector (430) within mount (420), resilient latches (438) may rotate along inner shelf (426) until reaching inner walls (428) which are configured to prevent resilient latches (438) from being rotated within receiving channel (421) any further. Once resilient latches (438) are positioned against inner walls (428) and thus adjacent to ramps (427), probe protector (430) may be withdrawn out from front-end opening (423) by exerting a proximal force on biopsy device (10) thereby causing resilient latches (438) to press against ramps (427). Ramps (427) cause resilient latches (438) to detent inwardly into elongate shaft (432) as resilient latches (438) are slidably translated along ramps (427) until completely removed from front-end opening (423).

Figure 8:
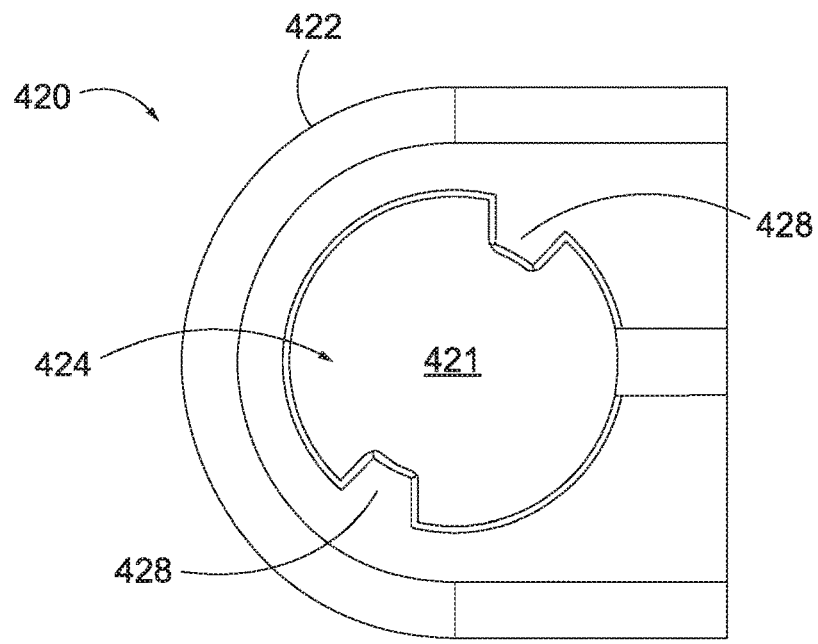
FIG. 8 depicts a rear elevation view of the device holder of FIG. 1.

As seen in FIG. 8, rear-end opening (424) does not include chamfered edge (425), inner shelf (426) or ramps (427). Therefore, inserting probe protector (430) through rear-end opening (424), rather than front-end opening (423), will not securely hold resilient latches (438) in receiving channel (421). Instead, in the event an operator inadvertently inserts probe protector (430) into mount (420) through rear-end opening (424), the operator will easily identify the mistake since biopsy device (10) will not be securely grasped by mount (420) due to the absence of chamfered edge (425), inner shelf (426), and ramps (427).

Figure 9A:
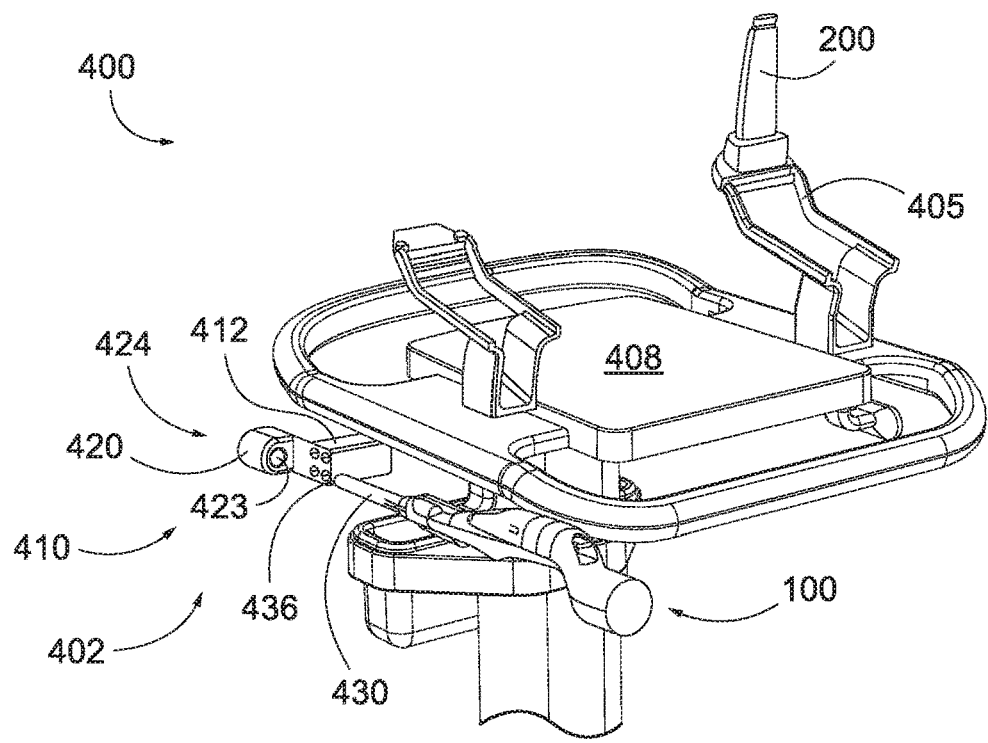
FIG. 9A depicts a partial perspective view of the control module cart of FIG. 1, with the probe protector coupled to the biopsy device and aligned for insertion into the device holder of FIG. 1.

As best seen in FIG. 9A, extension (412) extends device holder (410), and a biopsy device (10) held therein, out and away from cart surface (408) of control module cart (400) to thereby suspend device holder (410) and biopsy device (10) in air. By isolating device holder (410) and biopsy device (10) in air and away from cart surface (408), and from any other plane surfaces (not shown) in the procedure room, an operator may ensure biopsy device (10) wont inadvertently contact a non-sterile surface during the medical procedure.

In use, probe protector (430) may be preassembled onto biopsy device (10) such that needle (110) is contained within elongated shaft (432) at the onset to ensure the sterility of needle (110) is maintained. Probe protector (430) further serves to encase tissue piercing tip (112) within elongated shaft (432) to ensure tissue piercing tip (112) does not inadvertently contact a person and thereby cause bodily injury, or contact an object and thereby cause structural damage to tissue piercing tip (112). As will be described in greater detail below, an operator may mount biopsy device (10) to control module cart (400) through mount (420). In this instance, although not shown, biopsy device (10) may not yet include holster (200) securely coupled to probe (100). Instead, the operator may mount holster (200) onto holster holder (405) of control module cart (400). Holster holder (405) is configured to receive holster (200) to thereby maintain the sterility of holster (200) by separating holster (200) from cart surface (408). Furthermore, holster holder (405) maintains holster (200) in a mounted position to allow additional structural components to be installed onto holster (200) prior to biopsy device (10) being used in the biopsy procedure. By way of example only, the removable cover assembly referenced above and incorporated by reference herein may be installed onto holster (200) as holster (200) is securely held by holster holder (405). Once the removable cover assembly is securely attached to holster (200), holster (200) is removed from holster holder (405) and subsequently coupled to probe (100) of biopsy device (10).

Figure 9B:
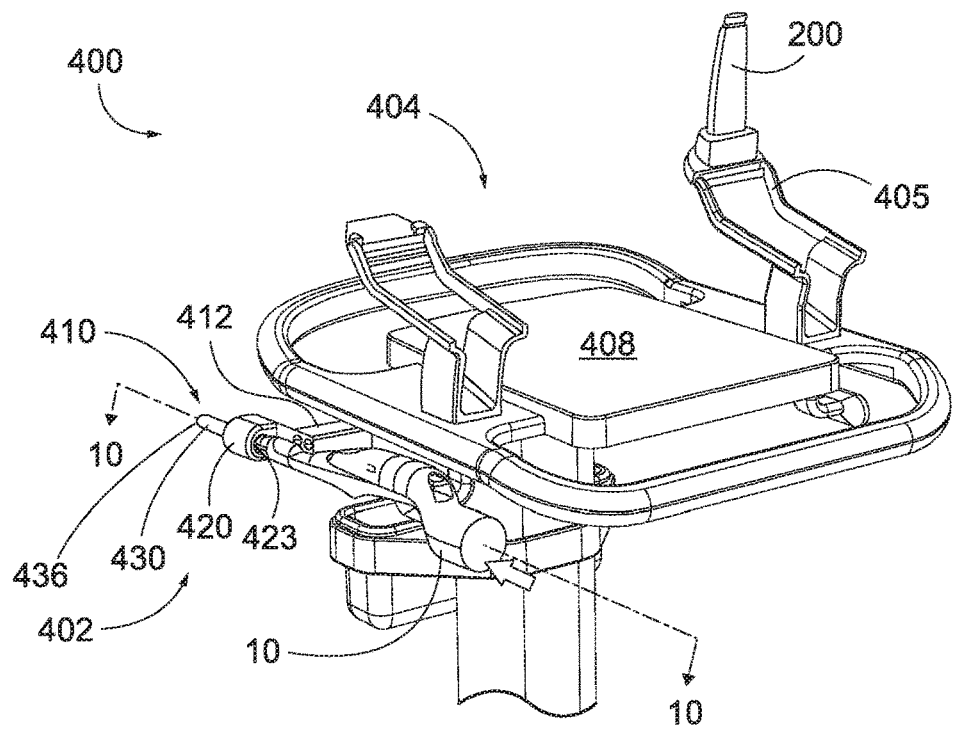
FIG. 9B depicts another partial perspective view of the control module cart of FIG. 1, with the probe protector coupled to the biopsy device and releasably secured to the device holder of FIG. 1.

Biopsy device (10), with probe protector (430) releasably attached at a distal end of biopsy device (10), is inserted into mount (420) as seen in FIG. 9A. During insertion, biopsy device (10) and probe protector (430) are initially aligned with receiving channel (421) of mount (420). Once aligned, biopsy device (10) and probe protector (430) are distally translated towards mount (420) until closed distal end (436) of probe protector (430) is advanced into front-end opening (423), through receiving channel (421), and out from rear-end opening (424), as seen in FIG. 9B. Although not shown, it should be understood that biopsy device (10) may be attached to device holder (410) before holster (200) is coupled to probe (100). In this instance, holster (200) is coupled to probe (100) with biopsy device (10) securely attached to mount (420).

FIGS. 10A-10D show the interaction between the interior components of mount (420) and probe protector (430) as the steps shown in FIGS. 9A-9D are performed. In an initial position, needle (110) of probe (100) is disposed within probe protector (430). In some examples, probe (100) is provided to an operator preassembled in sterile packaging with probe protector (430) pre-attached to needle (110). Accordingly, in the present use, an operator is not required to attach probe protector (430) to probe (100). Regardless, once probe protector (430) is attached probe (100) and probe (100) is attached to holster (200), the entire assembly is positioned adjacent to mount (420) with holster (200) positioned upwardly and probe (100) positioned downwardly as shown in FIG. 9A.

Figure 10A:
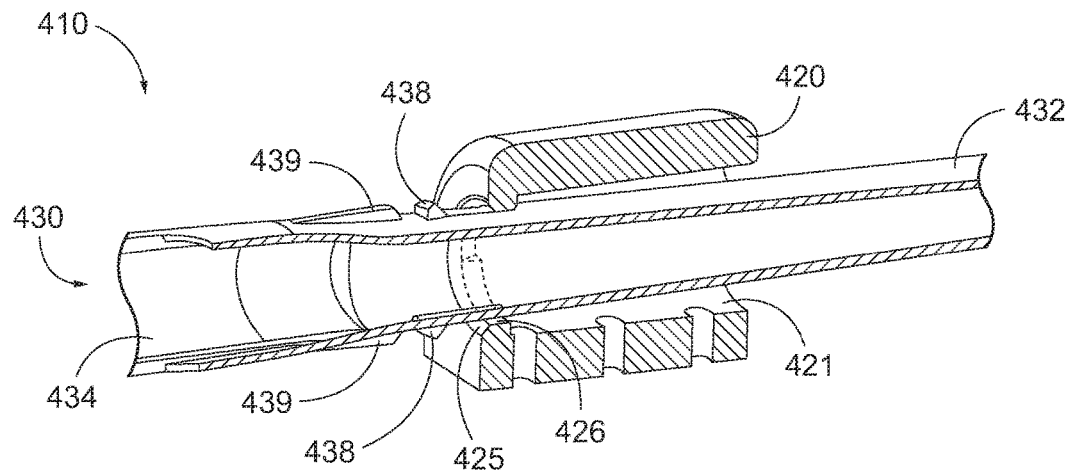
FIG. 10A depicts a partial perspective cross-sectional view of the device holder of FIG. 1, with the probe protector partially inserted into the device holder, with the cross-section taken along line 10-10 of FIG. 9B.

Once the assembly of probe protector (430), probe (100), and holster (200) is positioned adjacent to mount (420), an operator may insert probe protector (430) into mount (420). Probe protector (430) is next directed towards mount (420) as can be seen by comparing FIGS. 9A and 9B. During this transition, resilient latches (438) are directed towards chamfered edge (425) as shown in FIG. 10A. As resilient latches (438) engage chamfered edge (425), resilient latches (438) deform inwardly within probe protector (430) to permit further insertion of probe protector (430) into mount (420).

Figure 10B:
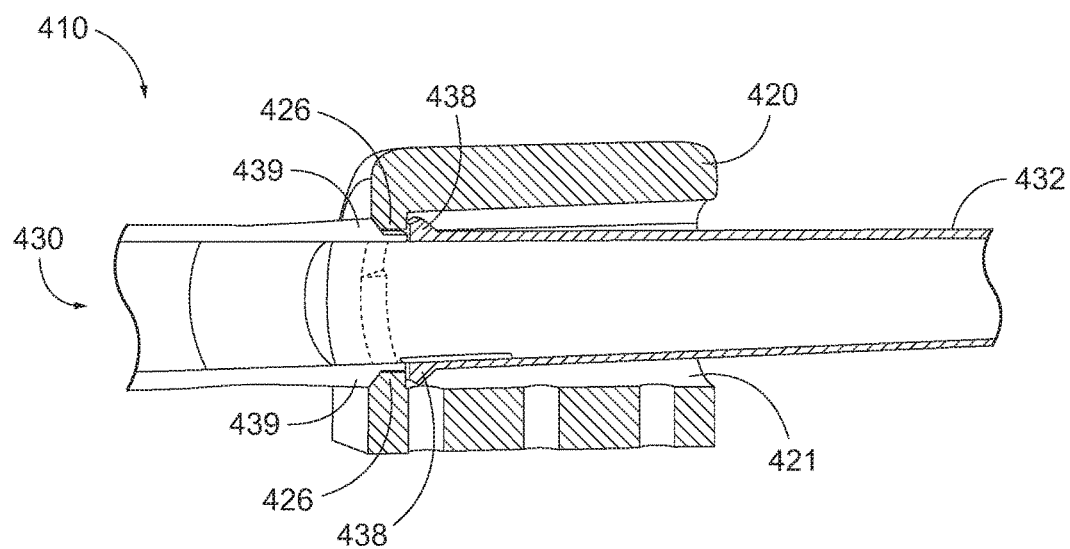
FIG. 10B depicts another partial perspective cross-sectional view of the device holder of FIG. 1, with the resilient latches of the probe protector releasably engaged by the inner shelf of the device holder, with the cross-section taken along line 10-10 of FIG. 9B.
Figure 11:
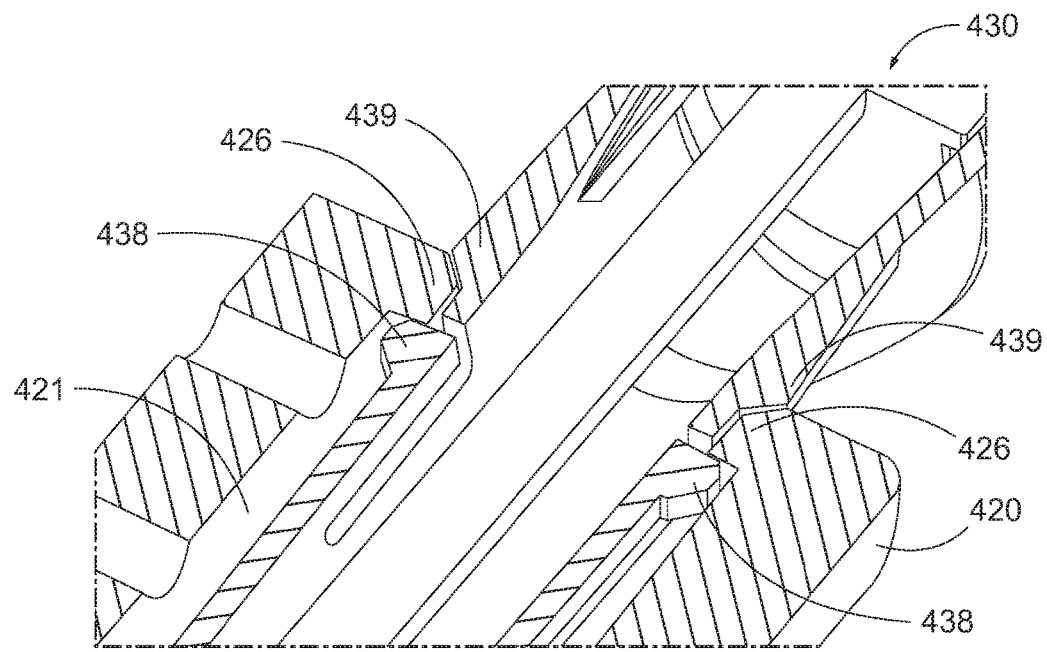
FIG. 11 depicts a partial perspective cross-sectional view of the device holder of FIG. 1, with the resilient latches and locking tabs of the probe protector engaged by the inner shelf of the device holder, with the cross-section taken along line 10-10 of FIG. 9B.

As seen in FIG. 10B, once resilient latches (438) are advanced past chamfered edge (425) and into receiving channel (421), resilient latches (438) resiliently deform outwardly and extend into receiving channel (421) to engage inner shelf (426) with locking tabs (439). In this instance, inner shelf (426) is securely maintained between locking tabs (439) and resilient latches (438), with locking tabs (439) positioned outside receiving channel (421) and resilient latches (438) positioned inside receiving channel (421), as best seen in FIG. 11. Locking tabs (439) prevent probe protector (430) from slidably translating further into receiving channel (421) beyond the position of locking tabs (439) along elongated shaft (432). Once resilient latches (438) and locking tabs (439) are engaged with inner shelf (426), resilient latches (438) and locking tabs (439) releasably secure probe protector (430) to mount (420) via the engagement of inner shelf (426) between resilient latches (438) and locking tabs (439). In this instance, resilient latches (438) are secured against a corner formed by inner shelf (426) and inner wall (428) within receiving channel (421). The corner formed by inner shelf (426) and inner wall (428) creates a hard stop against resilient latches (438) such that probe protector (430) is not able to rotate in that direction. As a result, probe protector (430) becomes securely locked into mount (420) to thereby securely maintain biopsy device (10) in device holder (410), as seen in FIG. 9B. Biopsy device (10) remains securely held by device holder (10) until an operator desires to remove biopsy device (10) for subsequent use in the biopsy procedure or disposal.

Figure 9C:
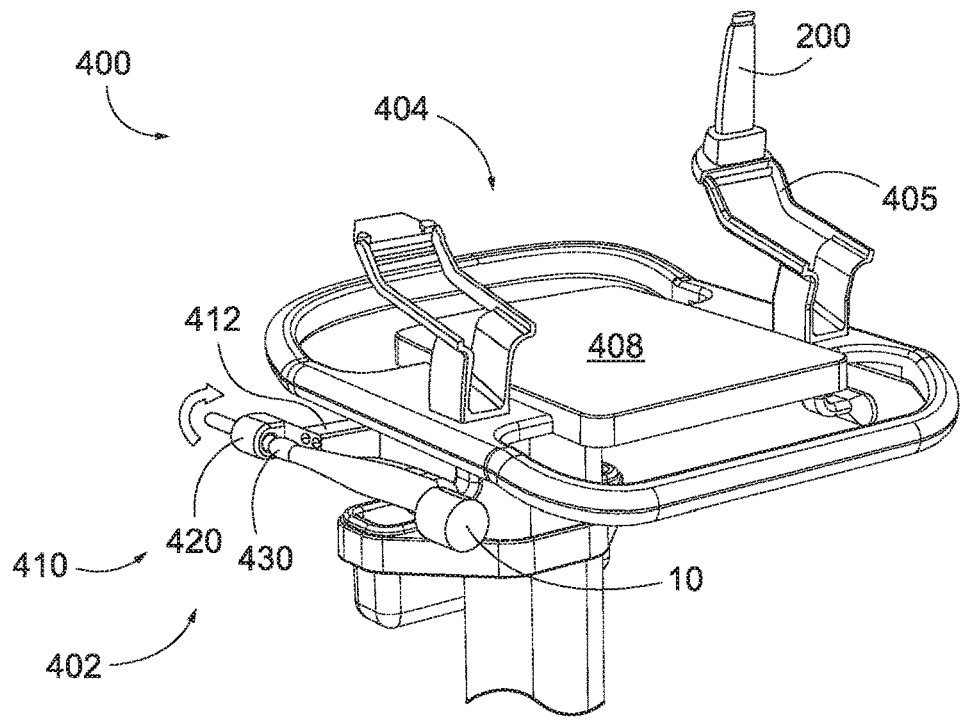
FIG. 9C depicts still another partial perspective view of the control module cart of FIG. 1, with the probe protector coupled to the biopsy device and the biopsy device rotated clockwise in the device holder of FIG. 1 to decouple the biopsy device from the device holder.
Figure 9D:
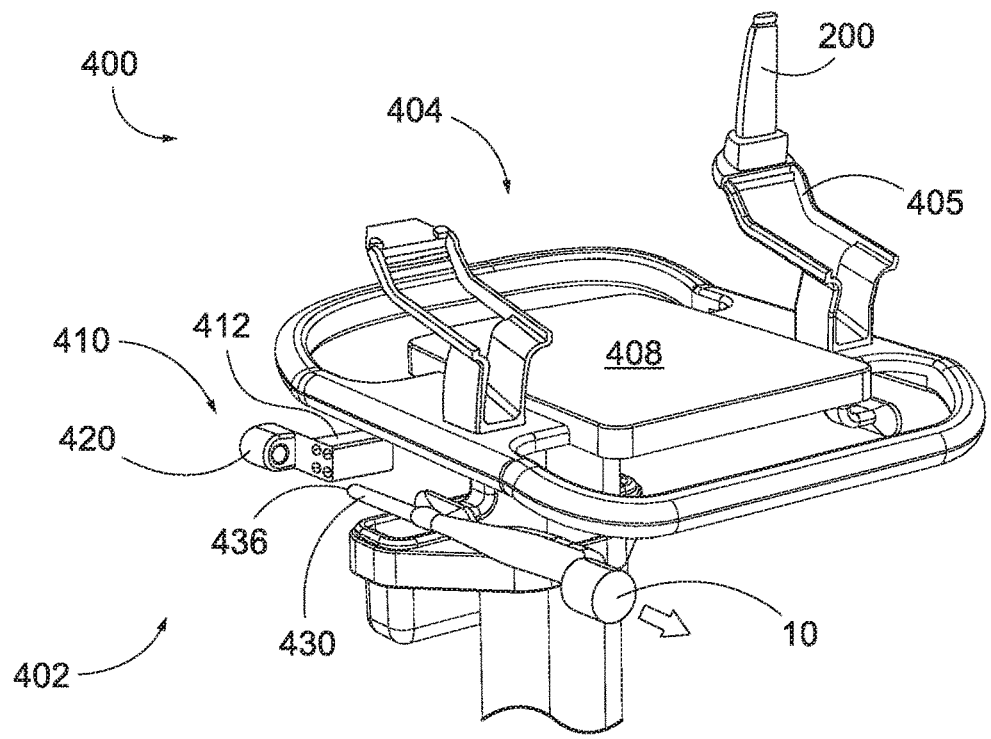
FIG. 9D depicts yet another partial perspective view of the control module cart of FIG. 1, with the probe protector coupled to the biopsy device and proximally removed from the device holder of FIG. 1 to release the biopsy device.
Figure 10C:
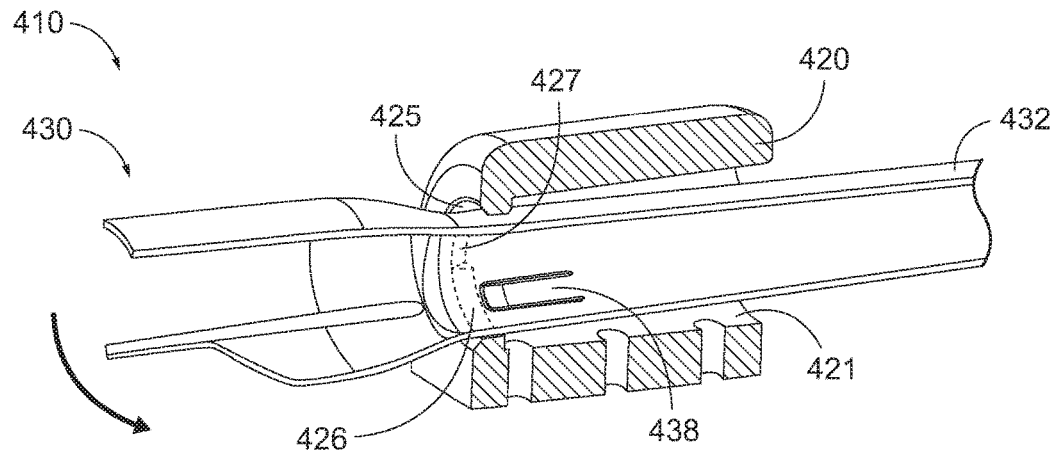
FIG. 10C depicts still another partial perspective cross-sectional view of the device holder of FIG. 1, with the probe protector rotated to align the resilient latches with ramps of the device holder, with the cross-section taken along line 10-10 of FIG. 9B.
Figure 10D:
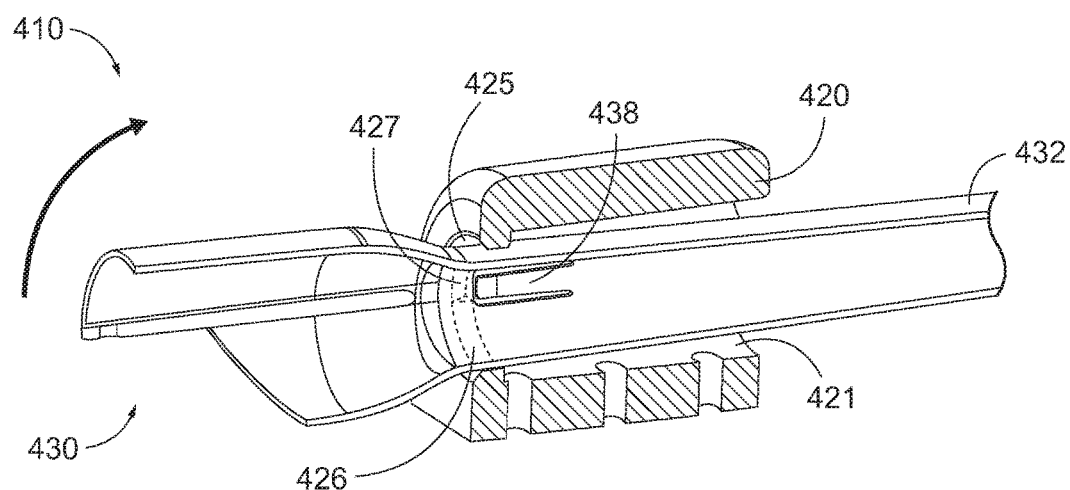
FIG. 10D depicts yet another partial perspective cross-sectional view of the device holder of FIG. 1, with the resilient latches of the probe protector aligned along the ramps of the device holder, with the cross-section taken along line 10-10 of FIG. 9B.

To remove biopsy device (10) from device holder (410), an operator can rotate biopsy device (10) in a first direction, as seen in FIG. 9C. Rotation of probe protector (430) directs resilient latches (438) along inner shelf (426) and away from the corner formed at inner shelf (426) and inner wall (428), as seen in FIG. 10C. As probe protector (430) is rotated in the first direction within receiving channel (421) resilient latches (438) are directed towards ramps (427) until becoming fully aligned with ramps (427), as seen in FIG. 10D. In this instance, an operator can exert a proximal force onto biopsy device (10) to deform resilient latches (438) inwardly into elongate shaft (432) and up along ramps (427). As seen in FIG. 9D, the proximal force results in the separation of probe protector (430) and biopsy device (10) from the releasable engagement with mount (920).

Figure 9E:
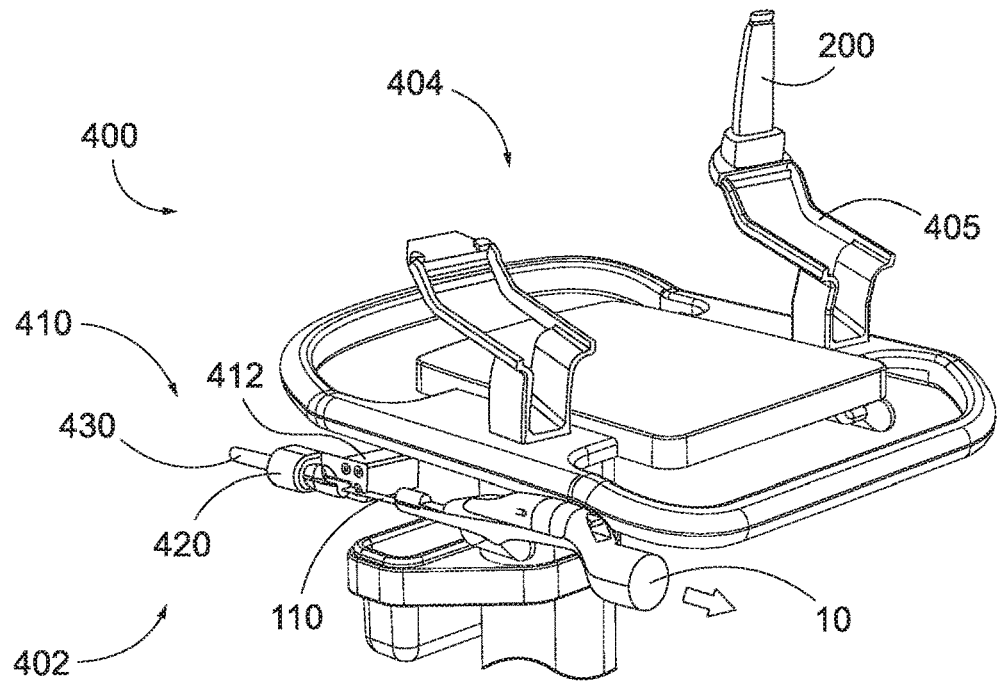
FIG. 9E depicts yet another partial perspective view of the control module cart of FIG. 1, with the probe protector coupled to the device holder and decoupled from the biopsy device, with the biopsy device proximally removed from the device holder of FIG. 1.

Prior to detaching both biopsy device (10) and probe protector (430) from mount (430), an operator may desire to simply remove biopsy device (10) from probe protector (430), as probe protector (430) remains secured to mount (430). As seen in FIG. 9E, this procedure generally occurs prior to rotating biopsy device (10) and probe protector (430) within mount (920) (as shown in FIG. 9C). During the procedure shown in FIG. 9E, an operator may exert a proximal force onto biopsy device (10) to overcome the resilient engagement between prongs (102) and notches (431) to thereby separate biopsy device (10) from the releasable engagement with probe protector (430). With biopsy device (10) removed from device holder (400), needle (110) is released from elongate shaft (432) with probe protector (430) remaining securely engaged with mount (920).

With biopsy device (10) freely maneuverable, an operator may utilize biopsy device (10) in the biopsy procedure as needle (110) is no longer contained within probe protector (430). In this instance, probe protector (430) remains securely coupled to mount (420) as biopsy device (10) is utilized by an operator. During the biopsy procedure, operator may desire to utilize a different surgical instrument and/or cease using biopsy device (10). In this instance, operator may seek to maintain the continued sterility of biopsy device (10) by inserting biopsy device (10) back into probe protector (430). With probe protector (430) still securely fastened to mount (420), an operator simply aligns needle (110) with open proximal end (434) and thereby advances biopsy device (10) distally towards probe protector (430) until prongs (102) and notches (431) engage one another. In this instance, prongs (102) engage notches (431) by snapping into notches (431) of probe protector (430).

At the conclusion of the biopsy procedure, an operator may desire to completely remove biopsy device (10) and probe protector (430) from control module cart (400). In this instance, as seen in FIG. 10D, probe protector (430) is rotated within receiving channel (421) until resilient latches (438) no longer abut against inner shelf (426) and instead are positioned adjacent ramps (427). Through rotation of probe protector (430) in mount (420), inner walls (428) ultimately direct resilient latches (438) towards ramps (427). An operator is able to identify when resilient latches (438) are rotatably aligned with ramps (427) through the inability to further rotate probe protector (430) within mount (420), created by the encounter between resilient latches (438) and inner walls (428). In this instance, an operator applies the predetermined opening force on biopsy device (10) in the proximal direction relative to mount (420) to thereby urge resilient latches (438) inwardly along ramps (427). As resilient latches (438) deform inwardly, ramps (427) direct resilient latches (438) proximally towards front-end opening (423) to thereby release probe protector (430) from mount (420). With biopsy device (10) released from device holder (10), an operator disengages holster (200) from probe (100) and thereby disposes biopsy device (10) and probe protector (430). Holster (200), being a reusable component, is positioned on holster holder (405) for later use.

Figure 12:
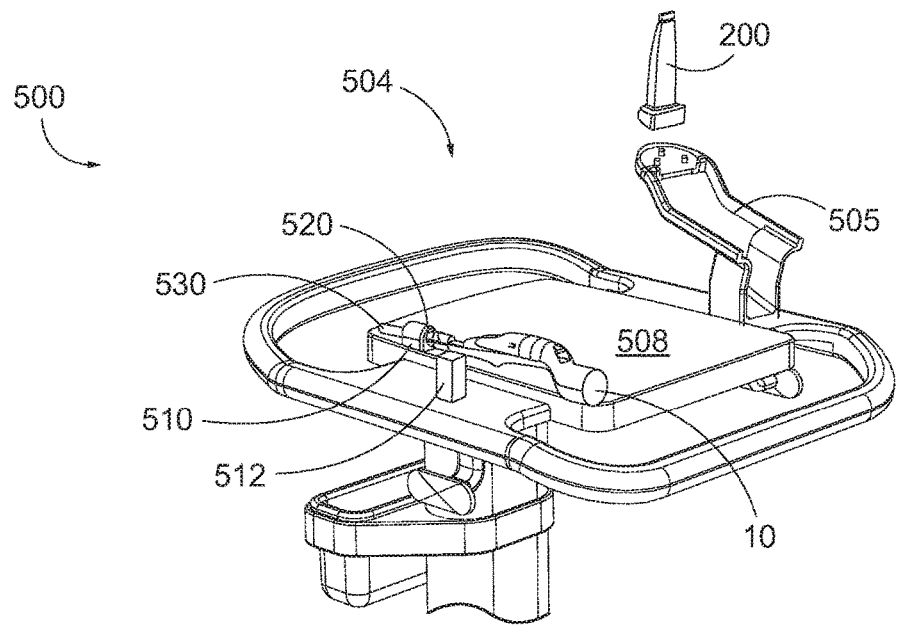
FIG. 12 depicts a perspective view of an exemplary alternative control module cart including an exemplary device holder mounted on a top surface.
Figure 13:
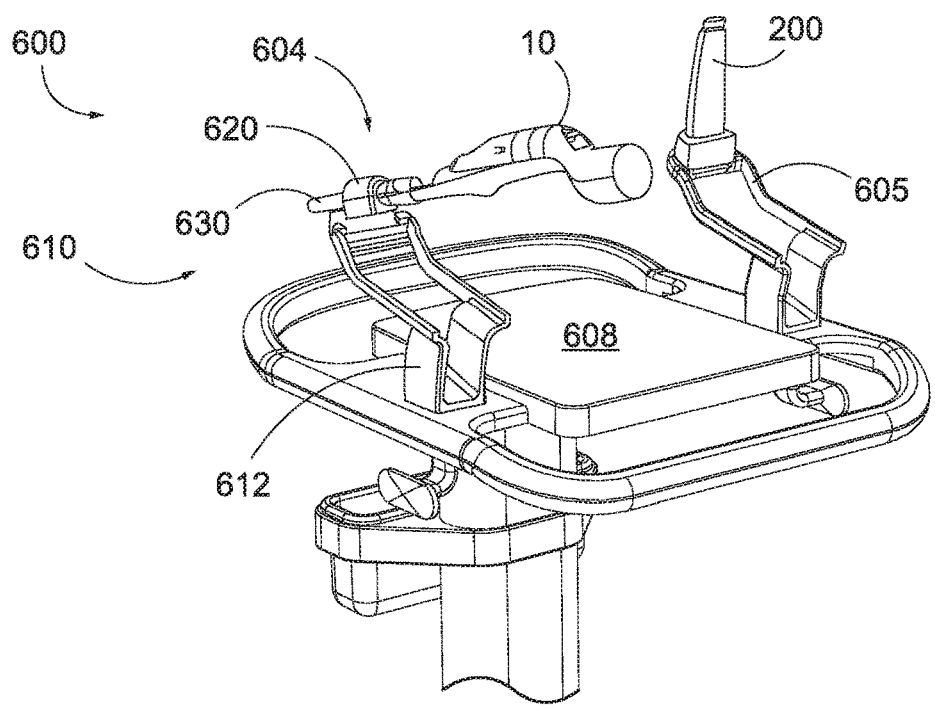
FIG. 13 depicts a perspective view of another exemplary alternative control module cart including an exemplary device holder alternatively mounted on a top surface.
Figure 14:
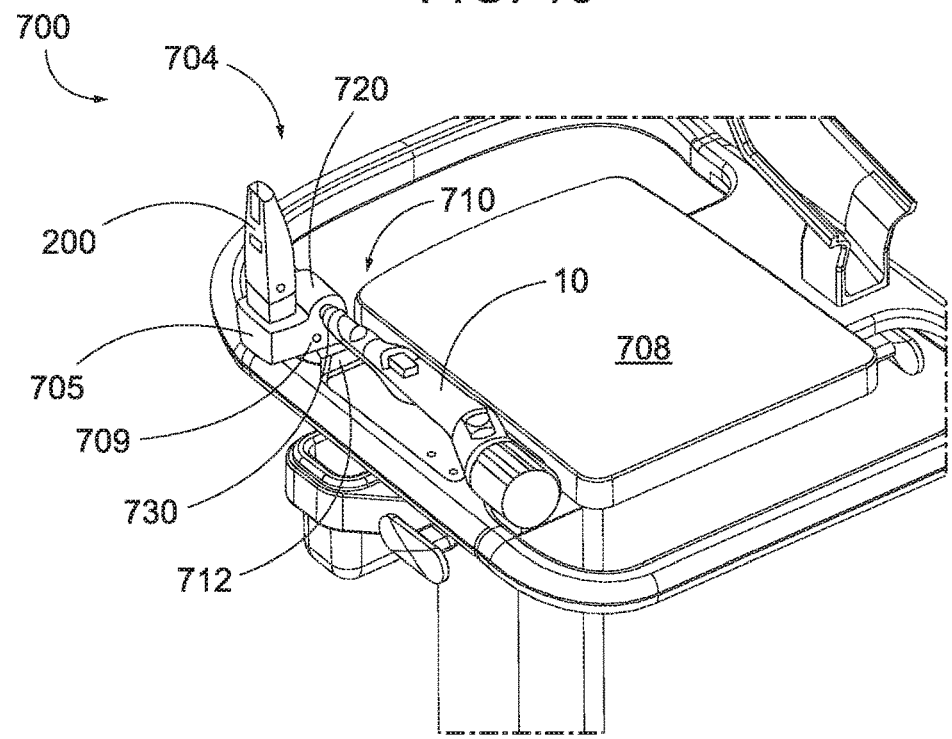
FIG. 14 depicts a perspective view of yet another exemplary alternative control module cart including an exemplary device holder alternatively mounted on a top surface with an exemplary holster holder.

FIGS. 12-15 illustrate exemplary alternative control module carts (500, 600, 700, 800) that may be used by an operator in various medical procedures. Control module carts (500, 600, 700) include, among other features and instrument holders, a device holder (510, 610, 710) extending upwardly from a top side (504, 604, 704) of control module cart (500, 600, 700), respectively. Control module cart (800) includes, among other features and instrument holders, a device holder (810) extending laterally from a left side (802) of control module cart (800). Device holders (510, 610, 710, 810) include an extension (512, 612, 712, 812), a mount (520, 620, 720, 820), and a probe protector (530, 630, 730, 830). As seen in FIGS. 12-14, extensions (512, 612, 712) are fixedly attached to control module carts (500, 600, 700), respectively, on a first end and extends longitudinally upward from top side (504, 604, 701) of control module carts (500, 600, 700).

Figure 15:
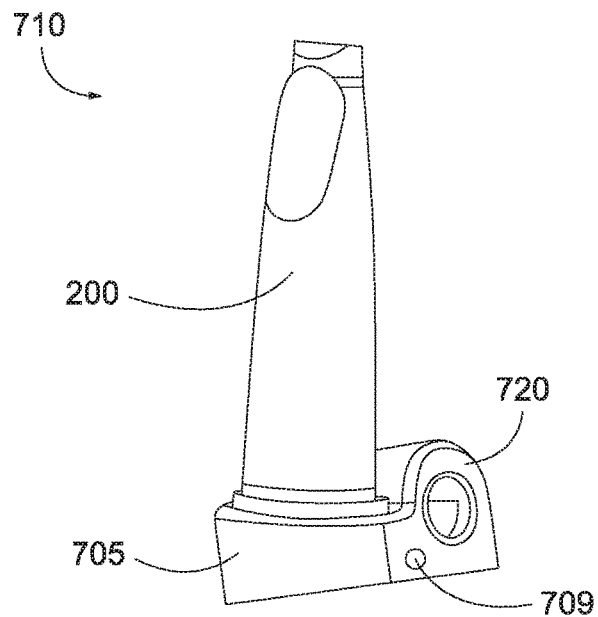
FIG. 15 depicts a perspective view of the device holder of FIG. 14, including a holster holder and a probe holder.

Device holder (710) further includes a probe-holder (709) positioned on mount (720), as seen in FIG. 15. Probe-holder (709) is configured to releasably receive needle (110) of biopsy device (10) to thereby hold biopsy device (10) on device holder (710) without probe protector (730) installed onto biopsy device (10).

Figure 16:
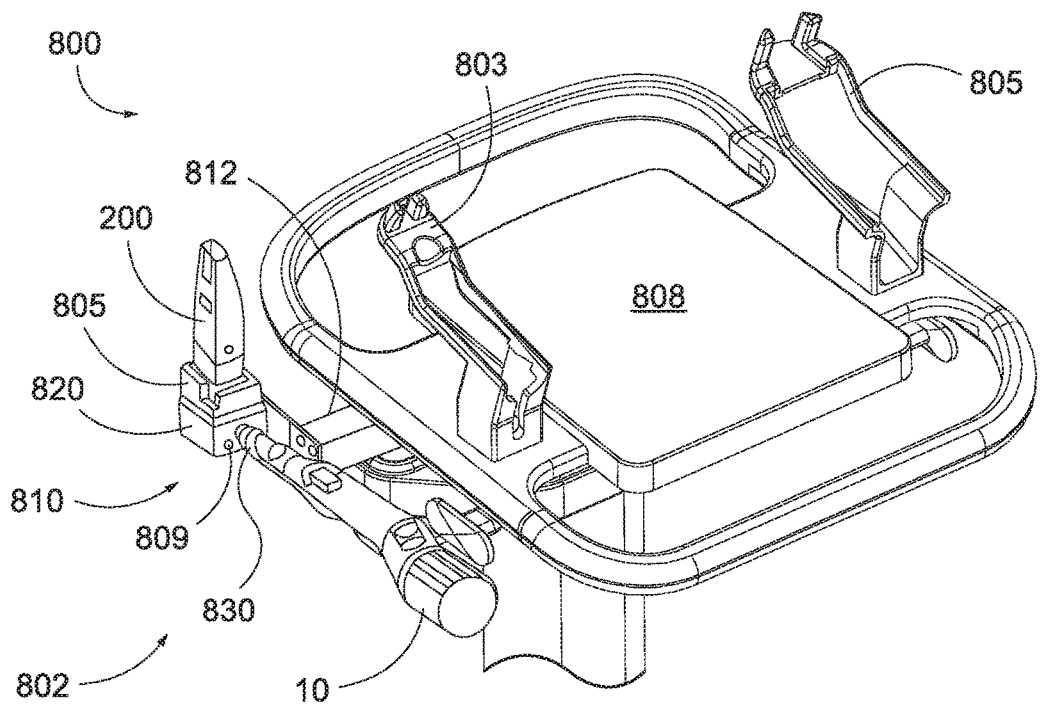
FIG. 16 depicts a perspective view of still another exemplary alternative control module cart including an exemplary device holder alternatively mounted on a left side with an exemplary holster holder.
Figure 17:
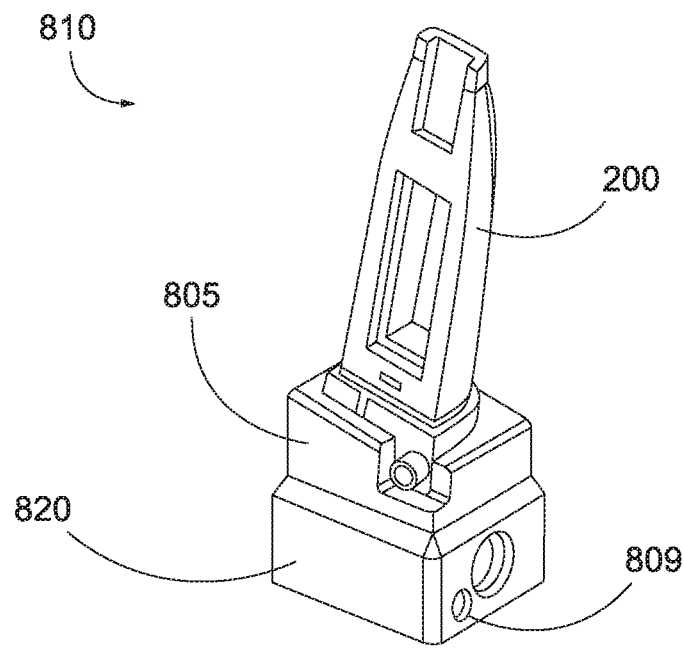
FIG. 17 depicts a perspective view of the device holder of FIG. 16, including a holster holder and a probe holder.

As seen in FIG. 16, device holder (810) extends outwardly from a left side (802) of control module cart (800). Extension (812) is fixedly attached to control module cart (800) on a first end and extends laterally from left side (802). In this instance, due to the position of device holder (810) and holster holder (805) along left side (802) of control module cart (800), control module cart (800) is configured to include a stereotactic holder (803) and an ultrasound holder (805) along a top side (804) of control module cart (800). Device holder (810) further includes a probe-holder (809) positioned on mount (820), as seen in FIG. 17. Probe-holder (809) is configured to releasably receive needle (110) of biopsy device (10) to thereby hold biopsy device (10) on device holder (810) without probe protector (830) installed onto biopsy device (10).

Mounts (520, 620, 720, 820) are fixedly attached to extensions (512, 612, 712, 812), respectively, on a second end, away from control module carts (500, 600, 700, 800). Mounts (520, 620, 720, 820) are suspended in air such that mounts (520, 620, 720, 820) are not in contact with any cart surfaces (508, 608, 708, 808) of control module carts (500, 600, 700, 800) or other plane surface (not shown) in the procedure room. Probe protectors (530, 630, 730, 830) are configured to be releasably received within mounts (520, 620, 720, 820), respectively, such that mounts (520, 620, 720, 820) are configured to hold probe protectors (530, 630, 730, 830) in physical isolation from extensions (512, 612, 712, 812), cart surfaces (508, 608, 708, 808), and other plane surfaces in the procedure room. Similar to control module cart (400), control module carts (500, 600, 700, 800) are configured to isolate device holders (510, 610, 710, 810) and biopsy device (10) in air and away from any plane surface so that an operator may ensure biopsy device (10) wont inadvertently contact a non-sterile surface during the medical procedure. Control module carts (500, 600, 700, 800) further include a holster holder (505, 605, 705, 805). As seen in FIGS. 12-13, holster holders (505, 605) extend longitudinally upward from top side (504, 604) of control module carts (500, 600). As seen in FIGS. 14 and 16, holster holders (705, 805) are integrally formed with mounts (720, 820) and extend longitudinally upward from mounts (720, 820), respectively. Holster holders (505, 605, 705, 805) are configured to receive holster (200) to thereby maintain the sterility of holster (200) by separating holster (200) from cart surfaces (508, 608, 708, 808).

Extensions (512, 612, 712, 812) extend mounts (520, 620, 720, 820), and a biopsy device (10) held therein, out and away from any cart surfaces (508, 608, 708, 808) of control module carts (500, 600, 700, 800) to thereby suspend biopsy device (10) in air. By isolating biopsy device (10) in air and away from cart surfaces (508, 608, 708, 808), and from other plane surfaces (not shown) in the procedure room, an operator may ensure biopsy device (10) wont inadvertently contact a non-sterile surface during the medical procedure. Holster holder (505, 605, 705, 805) receives holster (200) prior to an operator attaching holster (200) to biopsy device (10) to thereby maintain the sterility of holster (200) by separating holster (200) from cart surfaces (508, 608, 708, 808). Holster holder (505, 605, 705, 805) maintains holster (200) in a mounted position to allow additional structural components to be installed onto holster (200) prior to attaching holster (200) to biopsy device (10). During the biopsy procedure, an operator may determine that use of biopsy device (10) is desired or necessary. In this instance, holster (200) is selectively removed from holster holder (505, 605, 705, 805) and subsequently attached to biopsy device (10) as biopsy device (10) is securely held by mount (520, 620, 720, 820). Once holster (200) is securely attached to biopsy device (10), an operator exerts a proximal force relative to control module cart (500, 600, 700, 800) to disengage biopsy device (10) from probe protector (530, 630, 730, 830).

B. Probe Protector with Spiral Tabs

Figure 18:
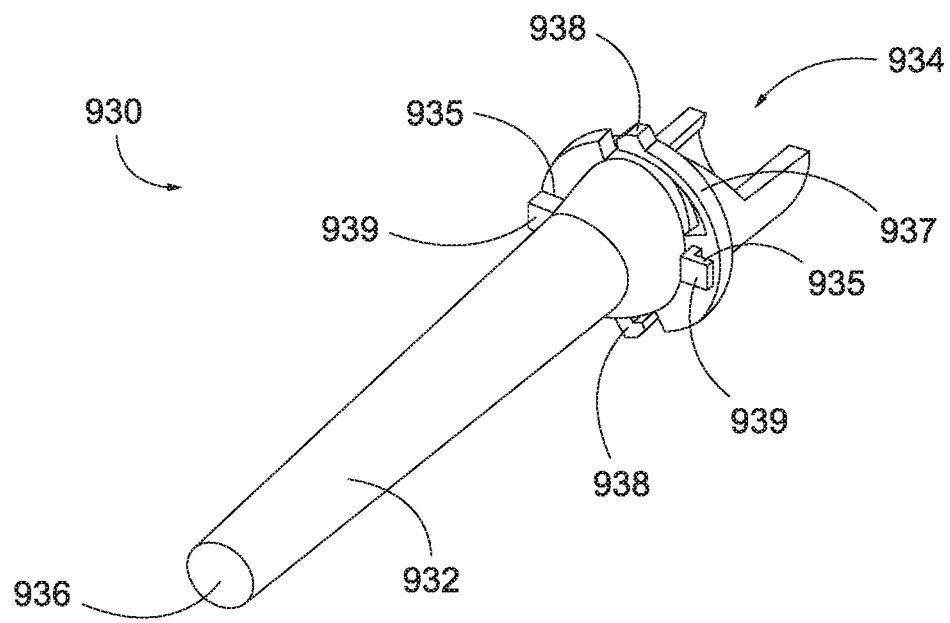
FIG. 18 depicts a perspective view of an exemplary alternative probe protector.
Figure 20:
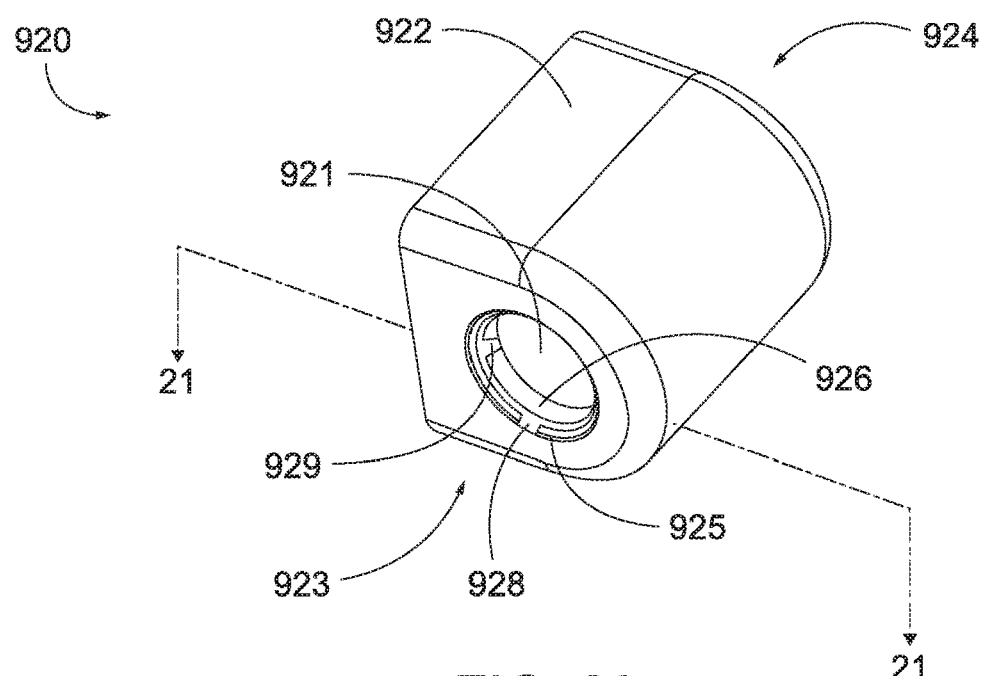
FIG. 20 depicts a perspective view of an exemplary alternative device holder.

FIG. 18 shows an exemplary alternative device holder (910) including a probe protector (930) and mount (920) (FIG. 20). Similar to device holder (410), at least a portion of device holder (910) is fixedly attached to a control module cart (not shown) and is suspended in air such that mount (920) is not in contact with any cart surfaces (not shown) or other plane surface (not shown) in the procedure room. Except as otherwise described below, device holder (910), mount (920) and probe protector (930) may be configured and operable substantially similarly to device holder (410), mount (420) and probe protector (430), respectively, described above. Probe protector (930) is an elongated housing configured to be releasably received within mount (920) such that mount (920) may hold probe protector (930) in physical isolation from any cart surfaces and other plane surfaces in the procedure room.

Probe protector (930) includes a proximal opening (934) and a closed distal end (936) separated by an elongate shaft (932). Probe protector (930) further includes a pair of resilient tabs (938) and a pair of locking tabs (939) along elongate shaft (932) and proximal to proximal opening (934). Resilient tabs (938) and locking tabs (939) are generally configured to engage at least a portion of mount (920) to selectively secure probe protector (930) to mount (920). Resilient tabs (938) and locking tabs (939) are proximal to a proximal opening (934) and are configured to releasably attach probe protector (930) to mount (920). Resilient tabs (938) and locking tabs (939) are positioned along elongate shaft (932) in relation to each other to thereby correspond with the position of tab receivers (928) and locking tab receivers (929), respectively, as will be described in greater detail below. By way of example only, as shown in FIG. 18, resilient tabs (938) are positioned along elongate shaft (932) at 90 degree angles relative to locking tabs (939). It should be understood, however, that resilient tabs (938) and locking tabs (939) may be configured along elongate shaft (932) at other suitable positions in relation to each other as will be apparent to those of ordinary skill in the art in view of the teachings herein. Although resilient tabs (938) and locking tabs (939) of the present example are shown as being integral to the exterior surface of elongate shaft (932), it should be understood that in other examples resilient tabs (938) and locking tabs (939) are configured as separate components. In addition, or in the alternative, it should be understood that resilient tabs (938) and locking tabs (939) may include numerous alternative geometric configurations in other examples. Alternatively, other suitable alternative configurations for resilient tabs (938) and locking tabs (939) will be apparent to those of ordinary skill in the art in view of the teachings herein.

Figure 19:
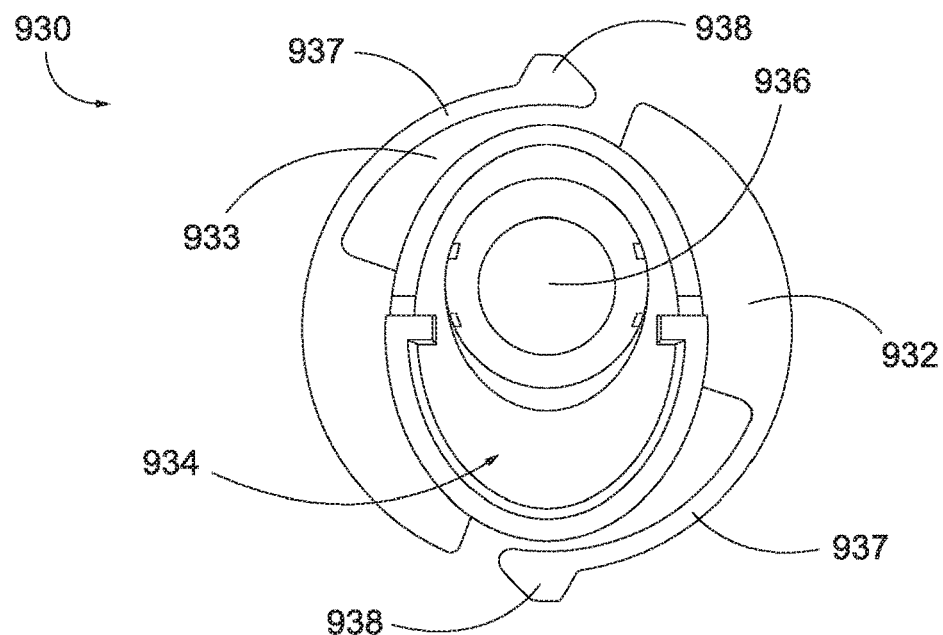
FIG. 19 depicts a rear elevational view of the probe protector of FIG. 18.

In the present example, locking tabs (939) extend outwardly from elongate shaft (932) and are configured to have a lateral configuration in relation to elongate shaft (932) to thereby separate locking tabs (939) from elongate shaft (932) by a static gap (935). As will be described in greater detail below, locking tabs (939) are configured to receive an inner shelf (926) of mount (920) when probe protector (930) is securely attached to mount (920). Resilient tabs (938) extend outwardly from elongate shaft (932) through flex arms (937) such that resilient tabs (938) are on a distal end of flex arms (937). As best seen in FIG. 19, flex arms (937) are configured to have a spiral configuration about elongate shaft (932) to thereby separate resilient tabs (938) from elongate shaft (932) by a variable gap (933). As will be described in greater detail below, flex arms (937) are configured to deflect resilient latches (938) inwardly into variable gap (933), and towards elongate shaft (932), when a lateral force is exerted upon resilient tabs (938).

FIG. 20 shows mount (920) including a receiving channel (921) positioned within an exterior housing (922) and extending between a front-end opening (923) and a rear-end opening (924). Front-end opening (923) includes a pair of tab receivers (928), an inner wall (925), an inner shelf (926) and a pair of locking tab receivers (929). Front-end opening (923) is configured to receive probe protector (930) and thereby direct closed distal end (936) and elongate shaft (932) through receiving channel (921) and out from rear-end opening (923).

Figure 21:
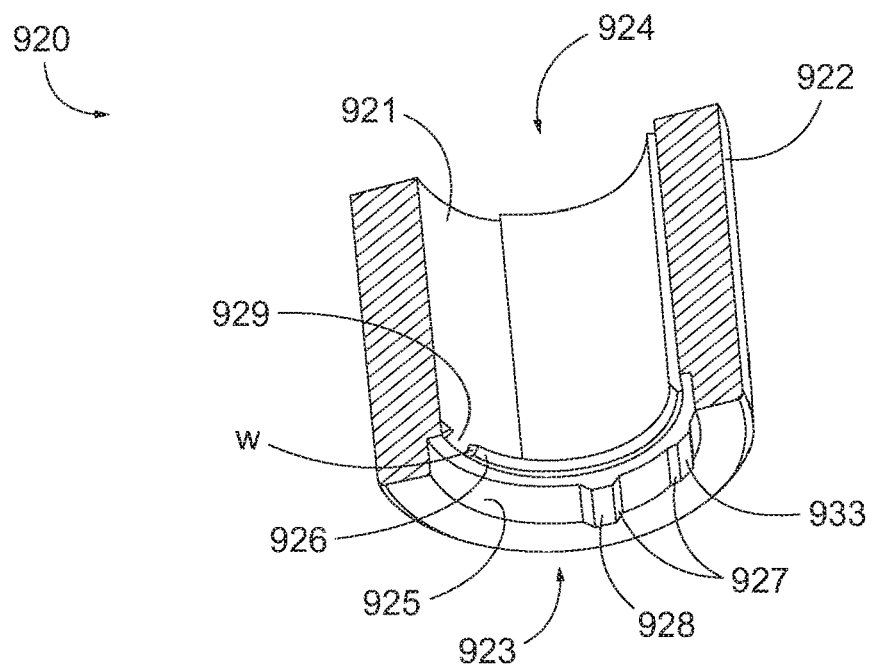
FIG. 21 depicts a perspective cross-sectional view of the device holder of FIG. 20, with the cross-section taken along line 21-21 of FIG. 20.

As best seen in FIG. 21, tab receivers (928) are positioned along the perimeter of front-end opening (923) and are configured to receive resilient tabs (938) into receiving channel (921) as probe protector (930) is slidably inserted into mount (920). In particular, tab receivers (928) are configured to receive resilient tabs (938) with flex arm (937) fully extended from elongate shaft (932) such that variable gap (933) is formed between elongate shaft (932) and resilient tabs (938). Tab receivers (928) are extended from the center of mount (920) at an extent greater than inner wall (925) such that inner wall (925) is configured to deform resilient tabs (938) inwardly into variable gap (933) and towards elongate shaft (932). Locking tab receivers (929) are positioned proximally relative to front-end opening (923) and are configured to receive locking tabs (939) along inner shelf (926) as probe protector (930) is slidably inserted into mount (920). In this instance, the size and shape of static gap (935) is configured to correspond to the lateral width (w) of inner shelf (926) such that locking tabs (939) are configured to receive inner shelf (926) within static gap (935).

In the present example, receiving channel (921) is configured to receive resilient tabs (938) along front-end opening (923) at tab receivers (928). Tab receivers (928) are positioned along front-end opening (923) to correspond with the position of resilient tabs (938). Tab receivers (928) include a side-ramp (927) that is configured to direct resilient tabs (938) along inner wall (925) and towards a tab securement (931) with the rotation of probe protector (930) within receiving channel (921). Tab receivers (928) include a single side-ramp (927) along a side of each tab receiver (928) closest to tab securement (931) such that resilient tab (938) is operable to enter and exit tab receiver (928) from only the side closest to tab securement (931). Tab securement (931) also includes a side-ramp (927) configured to receive resilient tab (938) into tab securement (931). Tab securement (931) includes a single side-ramp (927) along a side of tab securement (931) near to tab receiver (928) such that resilient tab (938) is operable to enter and exit tab securement (931) from only the side near tab receiver (928). As will be explained in greater detail below, side-ramps (927) of tab securements (931) are further configured to direct resilient tabs (938) out from tab securements (931) and toward tab receiver (928). Flex arms (937) are configured to bend towards elongate gate (932) to thereby deform resilient tabs (932) inwardly into variable gap (933) when a lateral force is exerted upon resilient tabs (938), such as the lateral force created by tab securement (931) as resilient tabs (938) are pressed against tab securement (931). With resilient tabs (938) wedged against tab securement (931), resilient tabs (938) are configured to selectably lock the rotational movement of probe protector (930) within mount (920).

Figure 22:
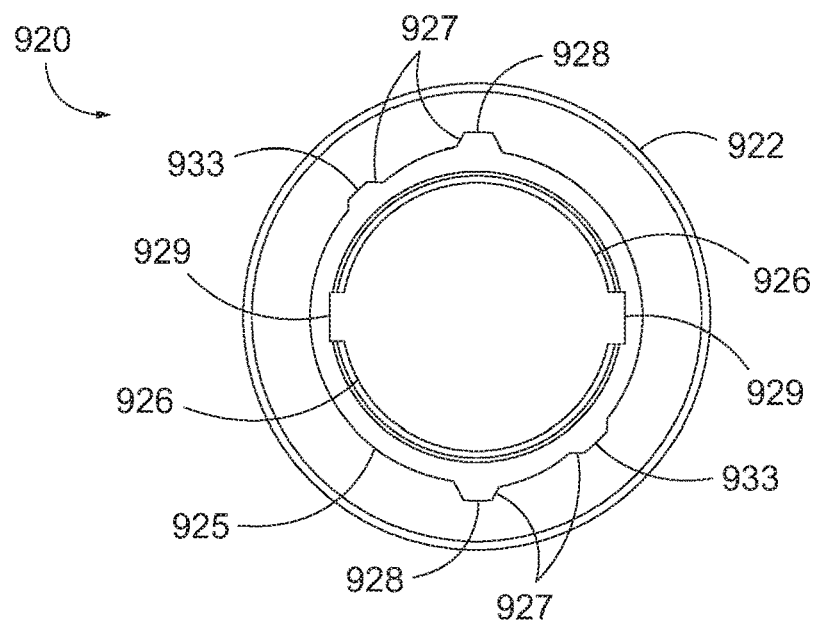
FIG. 22 depicts a front elevational view of the device holder of FIG. 20.

Receiving channel (921) is further configured to receive locking tabs (939) along front-end opening (923) at locking tab receivers (929). Locking tab receivers (939) are positioned along front-end opening (923) to correspond with the position of locking tabs (939). Tab receivers (928, 929) are further positioned along front-end opening (923) to correspond with the position of each other such that mount (920) simultaneously receives locking tabs (939) at locking tab receivers (929) and tab receivers (928) at resilient tabs (938). By way of example only, as shown in FIG. 22, tab receivers (928) are positioned along front-end opening (923) at 90 degree angles relative to locking tab receivers (929) to correspond with the location of tabs (938, 939) along probe protector (930). It should be understood, however, that tab receivers (928) and locking tab receivers (929) may be positioned around front-end opening (923) at other suitable positions in relation to each other as will be apparent to those of ordinary skill in the art in view of the teachings herein. Locking tab receivers (929) are configured to direct locking tabs (939) against inner shelf (926), with inner shelf (926) received within static gap (935), as probe protector (930) is rotated within receiving channel (921). With locking tabs (939) engaged against inner shelf (926), locking tabs (939) are configured to selectably lock the axial movement of probe protector (930) relative to mount (920). Thus, in collaboration with each other, tabs (938, 939) are cooperatively configured to couple probe protector (930) to mount (920) with probe protector (930) selectably rotated within receiving channel (921).

As seen in FIG. 22, inner wall (925) is positioned proximal to front-end opening (923) and extends uniformly along the whole perimeter of front-end opening (923) but for the locations of tab receivers (928). Similarly, inner shelf (926) is positioned proximal to front-end opening (923) and extends uniformly along the whole perimeter of front-end opening (923), but for the locations of locking tab receivers (929). Inner shelf (926) includes a flat surface oriented laterally relative to an axis defined between openings (923, 924). With probe protector (930) rotated to thereby engage the flat surface of inner shelf (926) within static gap (935), inner shelf (926) is generally configured to inhibit locking tabs (939) from being withdrawn from mount (920) by creating a physical barrier that is configured to catch against locking tabs (939). Thus, inner shelf (926) serves to axially secure probe protector (930) within mount (920) by inhibiting the slidable translation of locking tabs (939) out from receiving channel (921).

In the present example, probe protector (930) is inserted into mount (920) by aligning resilient tabs (938) with tab receivers (928), which thereby simultaneously aligns locking tabs (939) with locking tab receivers (929). With resilient tabs (938) received within receiving channel (921) at tab receivers (928), flex arms (937) remain fully extended such that variable gap (933) is formed between resilient tab (938) and elongate shaft (932). Simultaneously, with locking tabs (939) received within receiving channel (921) at locking tab receivers (929), inner shelf (926) is not positioned within static gap (935). By rotating probe protector (930) within mount (920) in a first direction, such as for example a counterclockwise direction, resilient tabs (938) rotate within receiving channel (921) from a received position within tab receiver (928) to an engaged position within tab securement (931). Side-ramps (927) of tab receivers (928) direct resilient tabs (938) from the received position within tab receivers (928) along inner walls (925). Side-ramps (927) of tab securement (931) direct resilient tabs (938) from inner walls (925) to the engaged position within tab securement (931). With resilient tabs (938) positioned against tab securement (931), resilient tabs (938) are forced inwardly into variable gap (933) wherein flex arms (927) deform inwardly to bend resilient tabs (938) toward elongate shaft (932). In this instance, tab securement (931) catches resilient tabs (938) to thereby selectably lock the rotational movement of probe protector (930) in relation to mount (920). Simultaneous with the rotation of resilient tabs (938) towards tab securement (931) is the rotation of locking tabs (939) within receiving channel (921) from a received position, with locking tabs (939) positioned at locking tab receiver (929), to an engaged position with locking tabs (939) slidably receiving inner shelf (926) within static gap (935). In this instance, locking tabs (939) selectably lock the axial movement of probe protector (930) in relation to mount (920).

Once resilient tabs (938) and locking tabs (939) are in their respective engaged positions, probe protector (930) becomes securely coupled to mount (920). In this instance, a proximal or distal exertion of force upon probe protector (930) will not effectively withdrawn probe protector (930) from the secured engagement with mount (920). Probe protector (930) may be withdrawn from mount (920) by rotating probe protector (930) in a second direction opposite of the first direction, such as for example a clockwise direction, to thereby rotate resilient tabs (938) and locking tabs (939) towards tab receiver (928) and locking tab receiver (929), respectively. With resilient tabs (938) directed away from tab securements (931) by side-ramps (927) and subsequently aligned with tab receiver (928), flex arm (937) deforms outwardly to thereby form variable gap (933) between resilient tab (938) and elongate shaft (932). Furthermore, with locking tab (939) aligned with locking tab receiver (929), inner shelf (926) is no longer positioned within static gap (935). In this instance, tab securement (931) and inner shelf (926) are not engaged with resilient tab (938) and locking tab (939), respectively, thus allowing probe protector (930) to be withdrawn distally from mount (920).

As seen in FIG. 21, rear-end opening (924) does not include inner wall (925), inner shelf (926) or receivers (928, 929). Therefore, inserting probe protector (930) through rear-end opening (924), rather than front-end opening (923), will not securely hold probe protector (930) in receiving channel (921). Instead, in the event an operator inadvertently inserts probe protector (930) into mount (920) through rear-end opening (924), the operator will easily identify the mistake since biopsy device (10) will not be securely grasped by mount (920) due to the absence of inner wall (925), inner shelf (926) or receivers (928, 929).

C. Probe Protector with Flange

Figure 23:
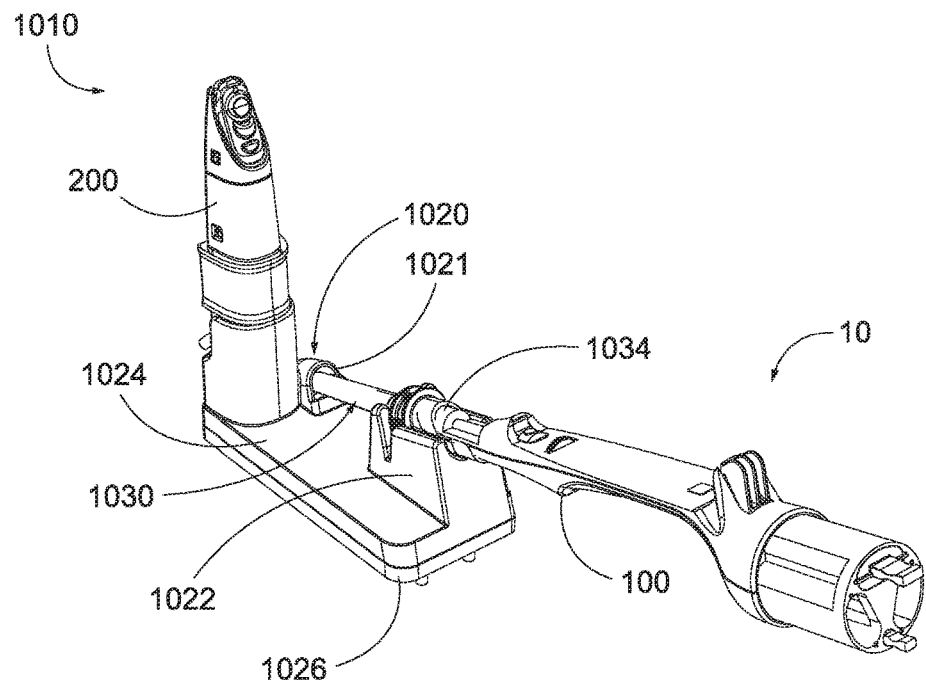
FIG. 23 depicts a perspective view of an exemplary alternative device holder and probe protector, with the probe protector engaged to a biopsy device and received within the device holder.

FIG. 23 shows an exemplary alternative device holder (1010) including a probe protector (1030), a mount (1020), and a stand (1022). Similar to device holder (410), at least a portion of device holder (1010) is fixedly attached to a control module cart (not shown) and is suspended in air such that mount (1020) and stand (1022) are not in contact with any cart surfaces (not shown) or other plane surface (not shown) in the procedure room. Except as otherwise described below, device holder (1010), mount (1020) and probe protector (1030) may be configured and operable substantially similarly to device holder (410), mount (420) and probe protector (430), respectively, described above. Device holder (1010) includes a top plate (1024) and a bottom plate (1026), with top plate (1024) positioned atop bottom plate (1026). As will be described in greater detail below, bottom plate (1026) is fixedly attached to the top surface of the control module cart and top plate (1024) is rotatably attached to bottom plate (1026). Mount (1020) is positioned on a distal end of top plate (1024) and stand (1022) is positioned on an opposite, proximal end of top plate (1024). As will be described in greater detail below, mount (1020) and stand (1022) are cooperatively configured to receive and hold probe protector (1030) on top plate (1024).

Figure 24:
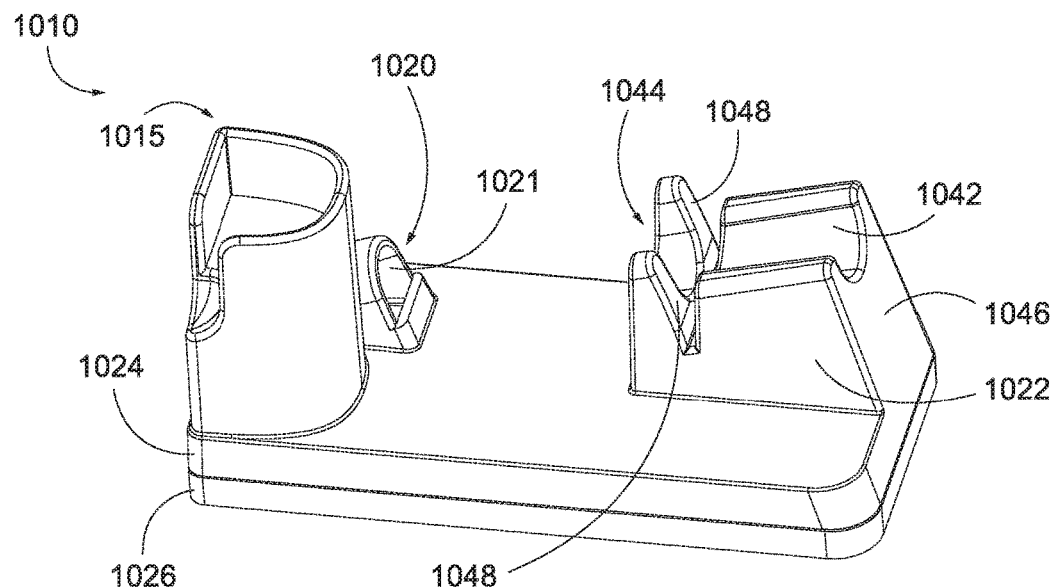
FIG. 24 depicts a perspective view of the device holder of FIG. 23.

Stand (1022) includes a channel (1042) extending between a distal end (1044) and a proximal end (1046), as best seen in FIG. 24. Channel (1042) is sized and shaped to have a semi-cylindrical profile to correspond to the elongated shape of probe protector (1030). As will be described in greater detail below, channel (1042) is configured to receive an elongated shaft (1032) of probe protector (1030). In some instances, channel (1042) also receives at least a portion of probe (100) of biopsy device (10) therein. Channel (1042) is aligned with opening (1021) of mount (1020) and comprises a downward slope extending between distal end (1044) and proximal end (1046). In other words, stand (1022) has an angled surface such that proximal end (1046) of channel (1042) is relatively higher than distal end (1044). As merely an illustrative example, channel (1042) is oriented at a 45° angle relative to top plate (1022). In other instances, channel (1042) can be oriented at an angle between 30° and 60°. In yet other instances, stand (1022) may be oriented at other slope angles for channel (1042) as will be apparent to those of ordinary skill in the art in view of the teachings herein.

As will be described in greater detail below, the sloped profile of channel (1042) is configured to align with opening (1021) of mount (1020) such that probe protector (1030) may be cooperatively received by both mount (1020) and stand (1022). Stand (1022) further includes a well (1048) positioned along channel (1042) adjacent to the distal end (1046). As will be described in greater detail below, well (1048) is sized and shaped to receive a flange (1038) of probe protector (1030) once mount (1020) receives the distal end of probe protector (1030). As will be described in greater below, stand (1022) is sized to extend from top plate (1024) at a predetermined height to thereby separate biopsy device (10) from top plate (1024) and any other cart surfaces of the control module cart (not shown).

Although not shown, it should be understood that in some examples well (1048) can be equipped with an elastomeric insert or coating. In such examples, a suitable elastomeric insert or coating can be configured to provide an interference fit between well (1048) and flange (1038) of probe protector (1030). As will be understood, such a feature may be desirable to retain probe protector (1030) within well (1048) to prevent inadvertent release of probe protector (1030) from stand (1022).

Mount (1020) includes an opening (1021) sized and shaped to receive a distal end (1036) of probe protector (1030), as will be described in greater detail below. More specifically, opening (1021) of mount (1020) is sized and shaped larger than distal end (1036) of probe protector (1030) such that the angular orientation of distal end (1036), and of probe protector (1030) as a whole, may be selectively adjusted within opening (1021). Stand (1022) is aligned on top plate (1024) with mount (1020) and is configured to receive a proximal end (1034) of probe protector (1030) when distal end (1036) is inserted into opening (1021).

Top plate (1024) of device holder (1010) further includes a holster holder (1015) positioned along the distal end of top plate (1024) adjacent to mount (1020). Holster holder (1015) extends towards a top side of the control module cart (not shown), away from any cart or plane surfaces that may be non-sterile. Similar to holster holder (405), holster holder (1015) is configured to receive and hold holster (200) therein. Mount (1020) is configured to hold distal end (1036) of probe protector (1030) in physical isolation from any cart surfaces and other plane surfaces in the procedure room, as seen in FIG. 23.

Figure 25:
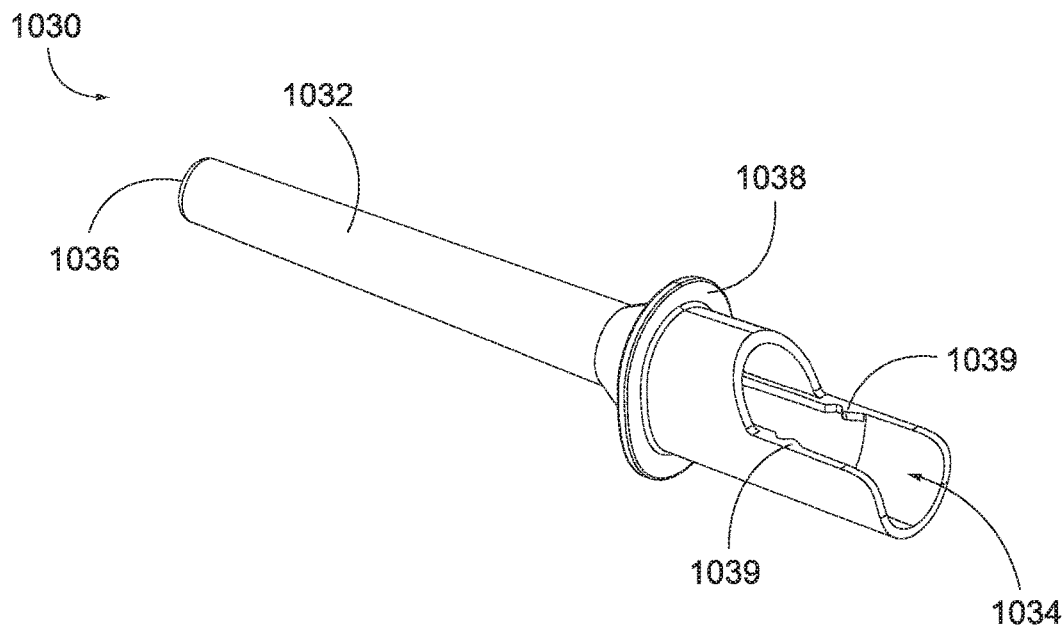
FIG. 25 depicts a perspective view of the probe protector of FIG. 23.

Probe protector (1030) is an elongated housing configured to be releasably received within mount (1020) and stand (1022). As best seen in FIG. 25, probe protector (1030) includes a proximal end or opening (1034) and a closed distal end (1036) separated by an elongate shaft (1032). Probe protector (1030) further includes a flange (1038) and a pair of notches (1039) along elongate shaft (1032), adjacent to proximal opening (1034). Notches (1039) are generally configured similar to notches (431) described above. In particular, track (101) of probe (100) is configured to receive and guide notches (1039) of probe protector (1030) towards prongs (102). Prongs (102) are configured to releasably secure biopsy device (10) to probe protector (1030) by engaging notches (1039) of probe protector (1030). In the present example, notches (1039) are sized and shaped to receive prongs (102) to thereby securely engage probe protector (1030) to probe (100). Prongs (102) and notches (1039) include corresponding chamfered surfaces such that prongs (102) and notches (1039) are cooperatively configured to disengage each other upon the application of a predetermined opening force. In this instance, urging probe protector (1030) in the distal direction relative to probe (100) and/or urging probe (100) in the proximal direction relative to probe protector (1030) effectively separates probe protector (1030) and probe (100) from an engaged position (see FIG. 26A) to a disengaged position (see FIG. 26C).

Notches (1039) are positioned along elongate shaft (1032) opposite in relation to distal end (1036) to thereby correspond with the position of prongs (102) of probe (100) when needle (110) is fully inserted into probe protector (1030) and tip (112) is adjacent to distal end (1036). Notches (1039) extend inwardly towards each other to thereby engage prongs (102) when biopsy device (10) is slidably inserted into probe protector (1030). It should be understood, however, that notches (1039) may be positioned along elongate shaft (1032) at other suitable positions in relation to prongs (102) of probe (100) as will be apparent to those of ordinary skill in the art in view of the teachings herein. Although notches (1039) of the present example are shown as being integral to probe protector (1030), it should be understood that in other examples notches (1039) are configured as separate components. In addition, or in the alternative, it should be understood that notches (1039) may include numerous alternative geometric configurations in other examples. Other suitable alternative configurations for notches (1039) will be apparent to those of ordinary skill in the art in view of the teachings herein.

Flange (1038) extends outwardly around the perimeter of elongate shaft (1032) and is configured to have a uniform, lateral extension in relation to elongate shaft (1032). In other words, flange (1038) extends along a plane that is oriented perpendicularly relative to a longitudinal axis defined by elongate shaft (1032). Although not shown, it should be understood that flange (1038) may extend along only a portion of elongate shaft (1032) or have a nonuniform extension from elongate shaft (1032). Flange (1038) is sized and shaped to correspond with, and be received within, well (148) of stand (1022). In other words, well (1048) is configured to receive and securely engage flange (1038) of probe protector (1030) when probe protector (1030) is securely attached to mount (1020) and lowered towards stand (1022).

Figure 26A:
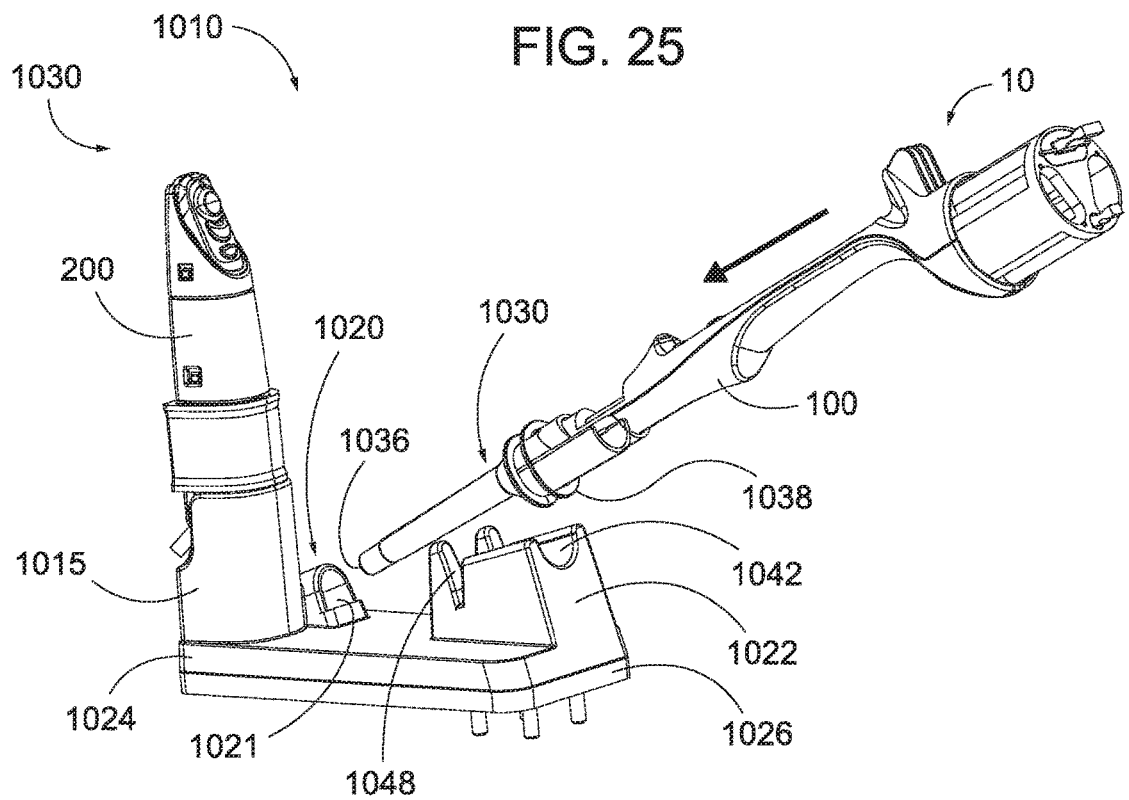
FIG. 26A depicts a perspective view of the device holder of FIG. 23 receiving the probe protector of FIG. 24, the probe protector attached to the probe of a biopsy device.
Figure 26B:
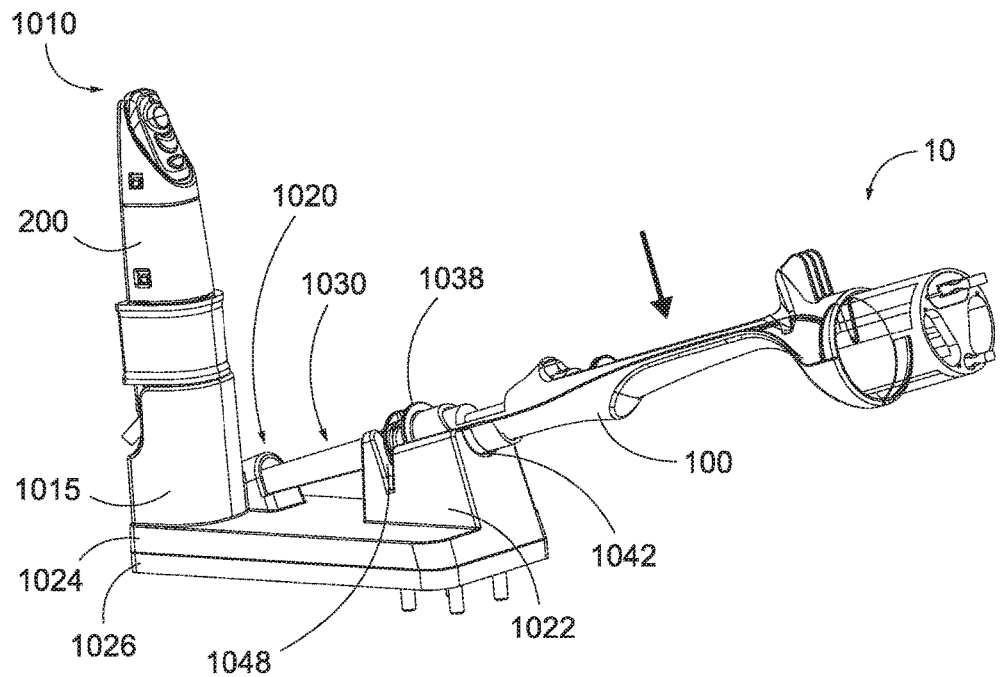
FIG. 26B depicts a perspective view of the device holder of FIG. 23 securely engaged with the probe protector.

In use, an operator places holster (200) onto holster holder (1015) to thereby install any protective components (not shown) or sterile sleeves (not shown) onto holster (200) as necessary. Probe protector (1030) is pre-attached to probe (100) of biopsy device (10) in a packaging (not shown) prior to use by an operator. Alternatively, probe protector (1030) may be manually assembled onto probe (100) by an operator. Upon removing the packaging, an operator utilizes device holder (1010) by inserting the assembly of probe protector (1030) and probe (100) (or biopsy device (10)) into mount (1020). In particular, as seen in FIG. 26A, closed distal end (1036) is directed towards opening (1021) at an angle so to avoid encountering stand (1022). With closed distal end (1036) securely received within opening (1021), an operator pivots probe (100) towards top plate (1024) with the engagement of distal end (1036) and mount (1020) serving as an anchor point. Probe (100) is drawn towards top plate (1024) until flange (1038) is firmly received within well (1048), as seen in FIG. 26B. Due to the configuration of holster holder (1015), mount (1020), and stand (1022), an operator is enabled to perform the steps described above with a single hand.

As described above, stand (1022) includes an angular profile such that probe (100) extends from device holder (1010) in a manner conducive for easy grasping by an operator. The extension of stand (1022) from top plate (1024) further ensures ample separation between biopsy device (10) and top plate (1024) and any other cart surface. The sloped configuration of channel (1042) of stand (1022) further enables an operator to grasp and utilize probe (100) of biopsy device (10) with a single hand.

Figure 26C:
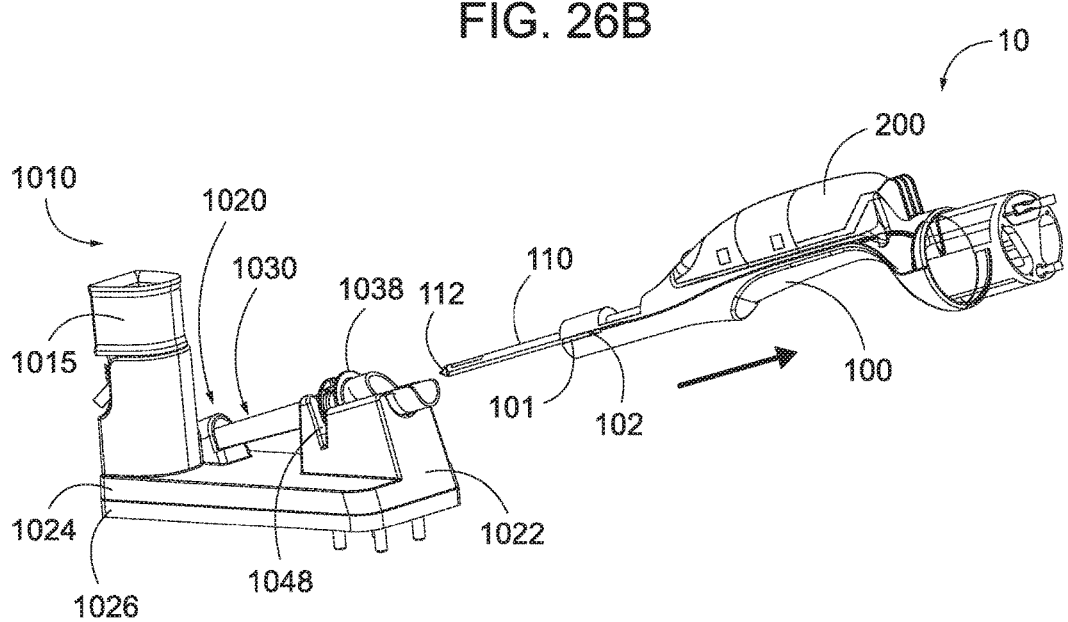
FIG. 26C depicts a perspective view of the device holder of FIG. 23, with the probe protector securely engaged therein and the biopsy device disengaged from the probe protector.

With biopsy device (10) securely engaged with device holder (1010), an operator removes holster (200) from holster holder (1015) and subsequently attaches holster (200) onto probe (100). In this instance, biopsy device (10) is fully assembled to perform a procedure. Once biopsy device (10) is fully assembled, an operator may desire to remove probe (100) from probe protector (1030) to perform a biopsy procedure. To remove probe (100) from probe protector (1030), an operator exerts a proximal force onto biopsy device (10) to overcome the resilient engagement between prongs (102) and notches (1039) to thereby disengage biopsy device (10) from the releasable engagement with probe protector (1030), as seen in FIG. 26C. The proximal force exerted by an operator is applied along an axis that is parallel to a longitudinal axis defined by elongate shaft (1032) of probe protector (1030). Particularly, with flange (1038) firmly secured within well (1048) of stand (1022), urging biopsy device (10) towards the proximal direction results in the disengagement of notches (1039) and prongs (102) of probe (100). With biopsy device (10) removed from device holder (1010), needle (110) is released from elongate shaft (1032) with probe protector (1030) remaining securely engaged with mount (1020) and stand (1022).

After probe (100) has been removed from probe protector (1030), an operator may utilize biopsy device (10) in a procedure as needle (110) is now uncovered from within probe protector (1030). Upon completion of the procedure, an operator reattaches biopsy device (10) to device holder (1010) by aligning needle (110) with proximal end opening (1034) and directing tip (112) into probe protector (1030). In other words, tip (112) of needle (110) is inserted into probe protector (1030) and towards closed distal end (1036) until prongs (102) and notches (1039) fittingly engage one another. In this instance, prongs (102) engage notches (1039) by snapping into notches (1039) of probe protector (1030). Probe (100) may be subsequently removed from probe protector (1030) and then reattached to probe protector (1030) as desired during the course of a biopsy procedure until the biopsy procedure is complete.

One the biopsy procedure is complete, an operator may desire to dispose of both probe (100) and probe protector (1030). Although not shown, it should be understood that prior to the process described below, an operator may remove holster (200) from probe (100) while probe (100) is coupled to probe protector (1030) to prepare probe (100) for disposal. For disposal, probe (100) and probe protector (1030) may be removed from device holder (1010) together as an assembly. In particular, as with the procedure described above for insertion of probe (100) and probe protector (1030) into device holder (1010), probe (100) is pivoted upwardly, relative to stand (1022). This pivoting motion results in probe protector (1030) being removed from channel (1042) while the continued engagement of closed distal end (1036) and mount (1020) serves as an anchor point. As probe protector (1030) and probe (100) are pivoted vertically away from stand (1022), and out of channel (1042), flange (1038) is simultaneously removed from well (1048), as shown in FIG. 26A. In this instance, with flange (1038) is no longer attached to well (1048) and elongate shaft (1032) is no longer received within channel (1042). Once flange (1038) is clear of well (1048), an operator is able to proximally pull or translate probe (100) relative to device holder (1010) to thereby remove closed distal end (1036) from opening (1021). As closed distal end (1036) evacuates mount (1020), biopsy device (10) becomes completely separated from device holder (1010).

Figure 27:
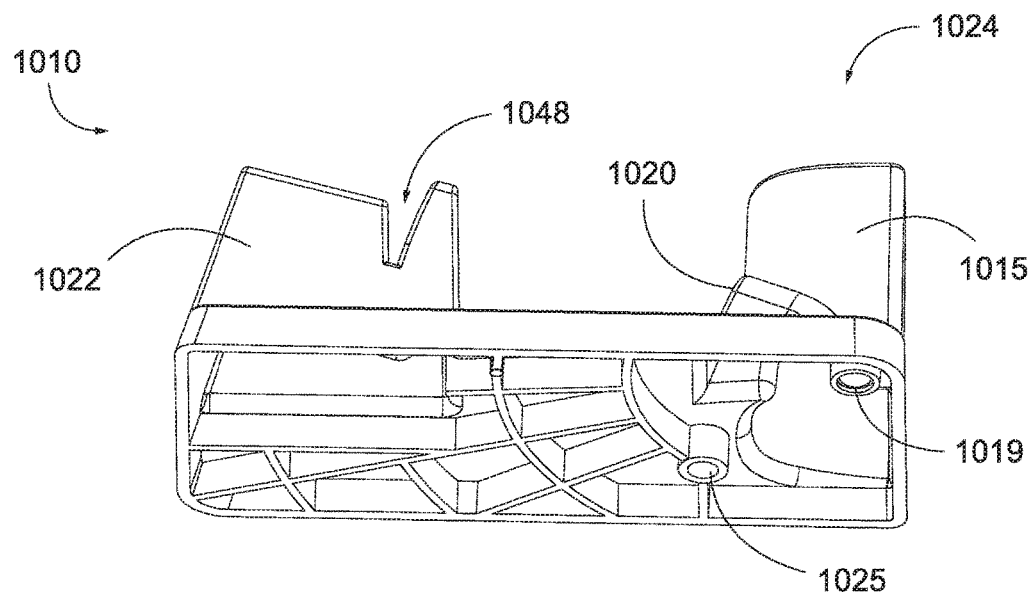
FIG. 27 depicts a perspective view of a top plate of the device holder of FIG. 23, with a bottom surface of the top plate including a ball detent.

In the present example, an operator may desire to adjust the angular position of device holder (1010) relative to the module cart surface (not shown) about a vertical axis to further distance and isolate the sterile surface that holds biopsy device (10), i.e. top plate (1024), from any non-sterile surfaces of the module cart. As discussed above, bottom plate (1026) is fixedly attached to the module cart, and top plate (1024) is configured to rotate relative to bottom plate (1026). As seen in FIG. 27, top plate (1024) includes a ball detent (1025) along a bottom surface such that ball detent (1025) is positioned between top plate (1024) and bottom plate (1026) when fully assembled together. Although not shown, it should be understood that ball detent (1025) may comprise other suitable forms or configurations to pivotably couple top plate (1024) to bottom plate (1026). By way of example only, ball detent (1025) may take the form of a screw, a resilient rubberized protrusion, a spring-loaded ball, a screw mechanism, or some other suitable feature as will be apparent to those of ordinary skill in the art. Top plate (1024) further includes a top slot (1019) passing through top plate (1024). As will be described in greater detail below, top slot (1019) is configured to align with a bottom slot (1023) of bottom plate (1026) to thereby attach top plate (1024) to bottom plate (1026).

Figure 28:
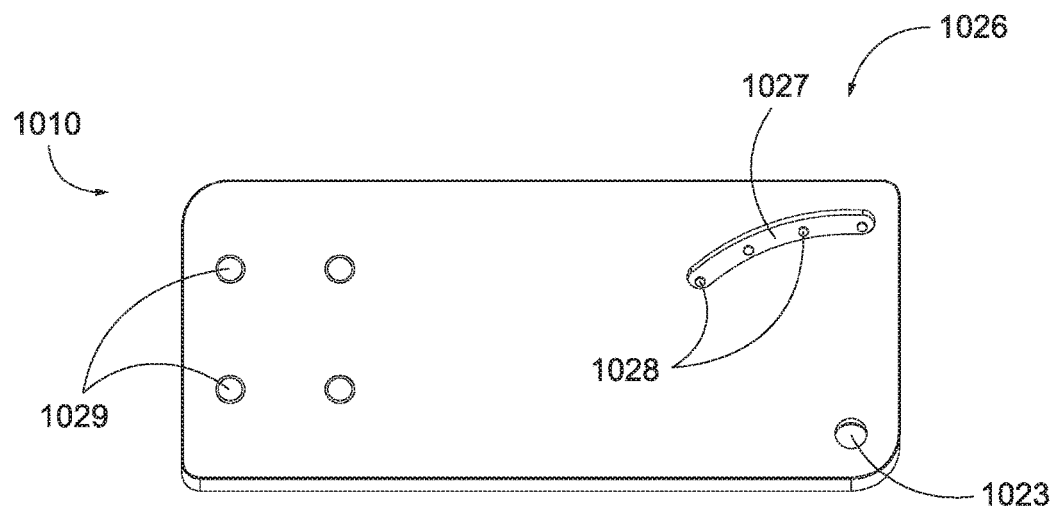
FIG. 28 depicts a perspective view of a bottom plate of the device holder of FIG. 23, with a top surface of the bottom plate including a track with multiple locking points positioned therein.

Ball detent (1025) is configured to be received within a track (1027) of bottom plate (1026), as best seen in FIG. 28. Track (1027) is located along a top surface of bottom plate (1026) and is configured to slidably receive ball detent (1025) therein to thereby enable top plate (1024) to pivotably couple to bottom plate (1026) about the relative position of ball detent (1025) in track (1027). Alternatively, it should be understood that ball detent (1025) may be attached to bottom plate (1026) and track (1027) may be correspondingly positioned along top plate (1024), respectively. Other corresponding positions and relationships between ball detent (1025) of top plate (1024) and track (1027) of bottom plate (1026) will be apparent to those of ordinary skill in the art in view of the teachings herein. Bottom plate (1026) further includes multiple connectors (1029) extending through bottom plate (1026) that are configured to fixedly attach bottom plate (1026) to the module cart surface, thereby securely fastening device holder (1010) to the module cart. In the present example, four connectors (1029) are shown. However, it should be understood that more or fewer connectors (1029) may be included on bottom plate (1026). The top surface of bottom plate (1026) includes a bottom slot (1023) that corresponds with top slot (1019) of top plate (1024). Bottom slot (1023) is configured to align with top slot (1019) when top plate (1024) is positioned atop bottom plate (1026) such that a fastening mechanism (not shown) secures top plate (1024) to bottom plate (1026) by passing through slots (1019, 1023). The fastening mechanism may comprise a screw, a bolt, a clip, or other suitable attachment feature as will be apparent to those of ordinary skill in the art. In other instances, slots (1019, 1023) may be excluded from plates (1024, 1026), respectively.

As further seen in FIG. 28, track (1027) is curved and includes multiple lock points (1028) along the length of track (1027). Lock points (1028) are configured to receive ball detent (1025) therein and releasably fix the orientation of top plate (1024) relative to bottom plate (1026) when ball detent (1025) is received within one of the lock points (1028). Although track (1027) is shown as being curved in the present example, it should be understood that track (1027) may comprise various shapes and/or profiles. Top plate (1024) is operable to align with bottom plate (1026) at as many angled orientations as the number of lock points (1028) included on track (1027). In the present example, track (1027) includes four lock points (1028) such that top plate (1024) is operable to align relative to bottom plate (1026) at four different orientations. Although four lock points (1028) are shown, it should be understood that more or fewer lock points (1028) may be included along track (1027) as will be apparent to those of ordinary skill in the art. By way of example only, lock points (1028) of track (1027) correspond to positioning top plate (1024) at the angles of 0°, 15°, 30° and 45°, respectively, relative to bottom plate (1026).

Figure 29A:
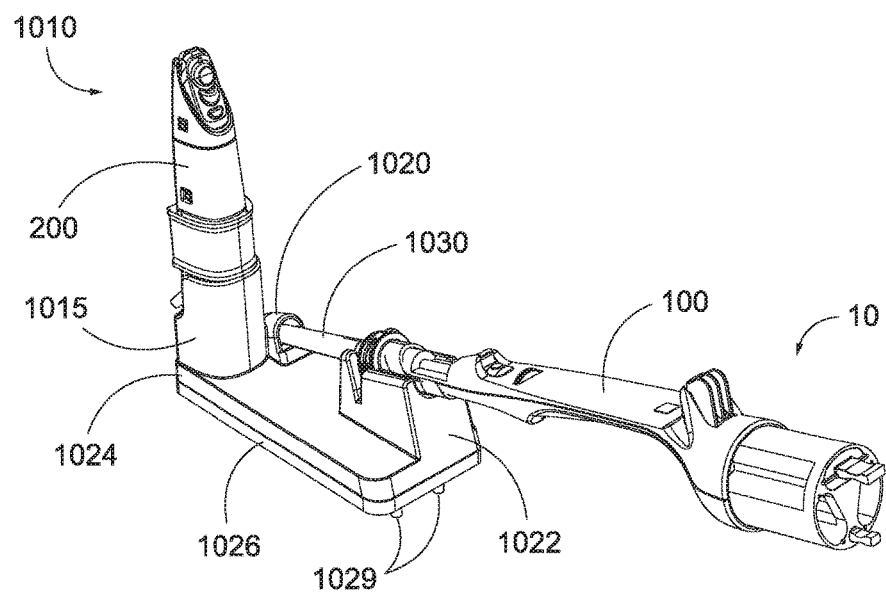
FIG. 29A depicts a perspective view of the device holder of FIG. 23 in a first position aligned with a bottom plate of a module cart.
Figure 29B:
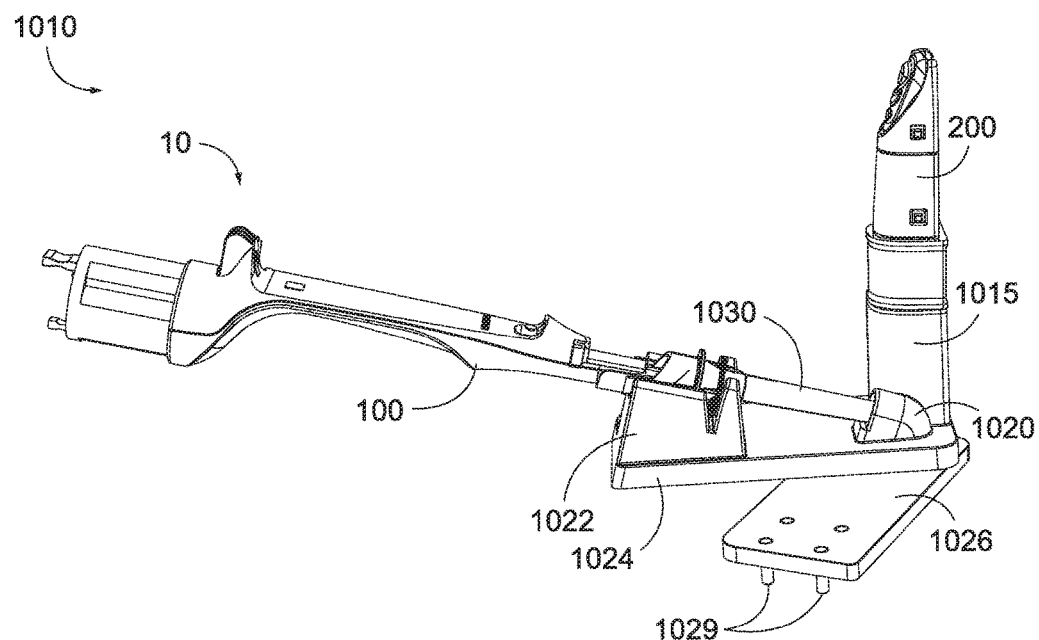
FIG. 29B depicts a perspective view of the device holder of FIG. 23 in a second position offset from the bottom plate of a module cart.

In use, as seen in FIG. 29A, top plate (1024) is completely aligned with bottom plate (1026) in a first position, i.e. at a 0° angle relative to bottom plate (1026), such that top plate (1024) does not extend beyond the footprint of bottom plate (1026). In other words, with top plate (1024) positioned atop bottom plate (1026) in the first position, top plate (1024) is not offset from the profile of the module cart's top surface (not shown). To selectively pivot top plate (1024) to a different orientation about a vertical axis, an operator firmly grasps top plate (1024) and exerts a lateral force thereon to disengage ball detent (1025) from the engagement with the current lock point (1028). In this instance, ball detent (1025) uncouples from the initial lock point (1028) and slides along track (1027) until encountering a subsequent lock point (1028) wherein ball detent (1025) securely engages the subsequent lock point (1028). An operator may continue to exert a lateral force onto top plate (1024) until top plate (1024) exhibits a desired orientation relative to bottom plate (1026). As seen in FIG. 29B, top plate (1024) is operable to rotate through each lock point (1028) of track (1027) such that holster holder (1015), mount (1020), and stand (1022) are incrementally repositioned relative to bottom plate (1026).

Figure 30:
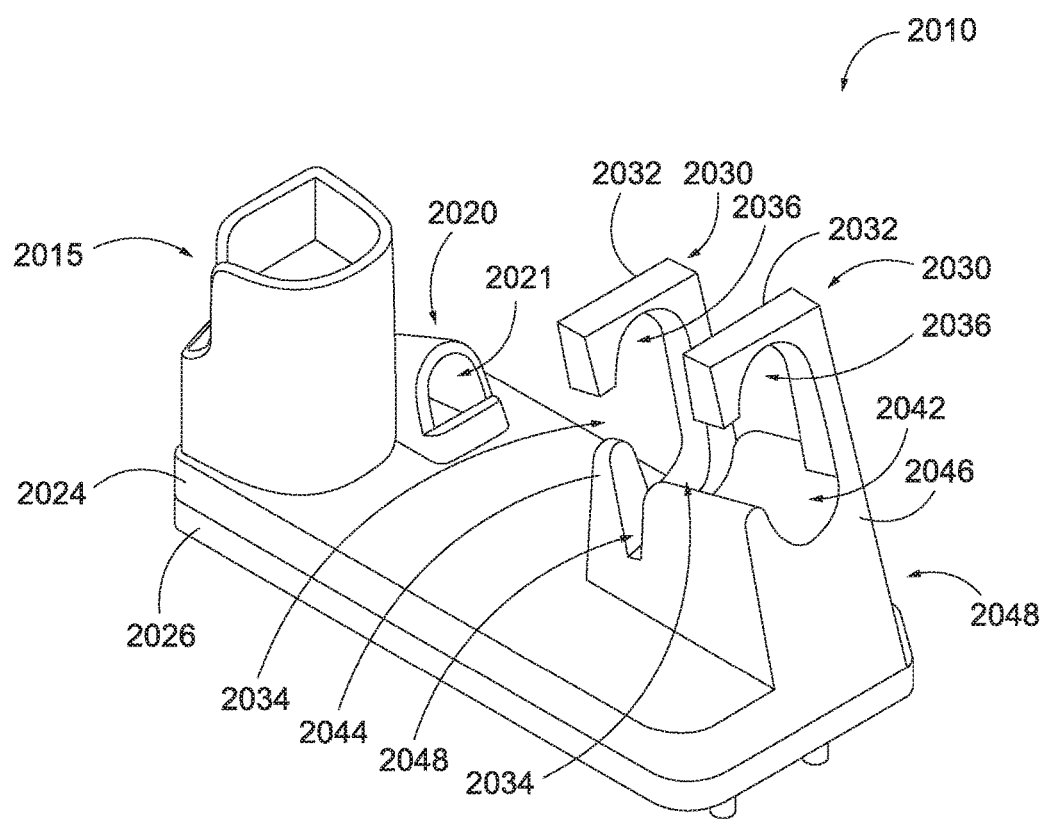
FIG. 30 depicts a perspective view of an exemplary alternative device holder for use with the probe protector of FIG. 23.

FIG. 30 shows an exemplary alternative device holder (2010) that is substantially similar to device holder (1010) described above. For instance, like with device holder (1010), device holder (2010) is usable with probe protector (1030) and includes a mount (2020), and a stand (2022). Similarly to device holder (1010), at least a portion of device holder (2010) is fixedly secured to a control module cart (not shown) and is suspended in air such that mount (2020) and stand (2022) are not in contact with any cart surfaces or other surfaces in the procedure room. Except as otherwise described below, device holder (2010) is configured and operable substantially similarly to device holder (1010) described above.

As with device holder (1010) described above, device holder (2010) includes a top plate (2024) and a bottom plate (2026) with top plate (2024) positioned on top of bottom plate (2026). Like with plates (1024, 1026) described above, plates (2024, 2026) are configured to secure device holder (2010) to a control module cart while still providing at least some pivoting movement of device holder (2010) relative to the control module cart to permit some selective repositioning. It should be understood that the features of top plate (2024) and bottom plate (2026) are substantially similar to corresponding features of tip plate (1024) and bottom plate (1026) described above, such that similar features will not be further described herein.

Mount (2020) is positioned on a distal end of top plate (2024) and stand (2022) is positioned on an opposite, proximal end of top plate (2024). As similarly described above with respect to mount (1020) and stand (1022), mount (2020) and stand (2022) of the present example are cooperatively configured to receive and hold probe protector (1030) on top plate (2024). Mount (2020) includes an opening (2021) sized and shaped to receive a distal end (1036) of probe protector (1030), as will be described in greater detail below. More specifically, opening (2021) of mount (2020) is sized and shaped larger than distal end (1036) of probe protector (1030) such that the angular orientation of distal end (1036), and of probe protector (1030) as a whole, may be selectively adjusted within opening (2021). Stand (2022) is aligned on top plate (2024) with mount (2020) and is configured to receive a proximal end (1034) of probe protector (1030) when distal end (1036) is inserted into opening (2021).

Stand (2022) includes a channel (2042) extending between a distal end (2044) and a proximal end (2046). Channel (2042) is sized and shaped to have a semi-cylindrical profile to correspond to the elongated shape of probe protector (1030). As will be described in greater detail below, channel (2042) is configured to receive an elongated shaft (1032) of probe protector (1030). In some instances, channel (2042) also receives at least a portion of probe (100) of biopsy device (10) therein. Channel (2042) is aligned with opening (2021) of mount (2020) and comprises a downward slope extending between distal end (2044) and proximal end (2046). In other words, stand (2022) has an angled surface such that proximal end (2046) of channel (2042) is relatively higher than distal end (2044). As merely an illustrative example, channel (2042) is oriented at a 450 angle relative to top plate (2022). In other instances, channel (2042) can be oriented at an angle between 30° and 60°. In yet other instances, stand (2022) may be oriented at other slope angles for channel (2042) as will be apparent to those of ordinary skill in the art in view of the teachings herein.

The sloped profile of channel (2042) is configured to align with opening (2021) of mount (2020) such that probe protector (1030) may be cooperatively received by both mount (2020) and stand (2022). Stand (2022) further includes a well (2048) positioned along channel (2042) adjacent to the distal end (2046). As will be described in greater detail below, well (2048) is sized and shaped to receive flange (1038) of probe protector (1030) once mount (2020) receives the distal end of probe protector (1030). As will be described in greater below, stand (2022) is sized to extend from top plate (2024) at a predetermined height to thereby separate biopsy device (10) from top plate (2024) and any other cart surfaces of the control module cart (not shown).

Top plate (2024) of device holder (2010) further includes a holster holder (2015) positioned along the distal end of top plate (2024) adjacent to mount (2020). Holster holder (2015) extends towards a top side of the control module cart (not shown), away from any cart or plane surfaces that may be non-sterile. Similar to holster holder (1015), holster holder (2015) is configured to receive and hold holster (200) therein.

Unlike stand (1022) described above, stand (2022) of the present example includes one or more retainers (2030) extending upwardly from a surface of stand (2022). Retainers (2030) in the present example are generally configured to retain probe protector (1030) within stand (2022) to prevent probe protector (1030) from being inadvertently released from stand (2022). In the present example, each retainer (2030) includes an overhang (2032) that is oriented over the channel (2042) of stand (2022). Overhang (2032) defines a lateral opening (2034) on a single side of stand (2022) to permit entry and egress of probe protector (1030) as will be described in greater detail below.

Overhang (2032) of each retainer (2030) defines an upwardly oriented recess (2036). Recess (2036) provides overhang (2032) with a generally c-shaped cross-section. In the present example, this cross-sectional shape can provide additional protection against probe protector (1030) from being inadvertently released from stand (2022). For instance, with the presence of recesses (2036), probe protector (1030) can only be removed from stand (2022) when oriented at a specific vertical position and horizontal position. Of course, it should be understood that recess (2036) is merely optional and that in some examples overhang (2032) is merely a flat surface.

Although the present example is shown as including two discrete retainers (2030), it should be understood that in other examples, retainers (2030) can have various alternative configurations. For instance, in some examples the two retainers (2030) shown can be joined into essentially a single retainer (2030). In other examples, device holder (2010) can include three or more retainers (2030). In still other examples, device holder (2010) can include a single retainer structured as a single one of the retainers (2030) shown but centered on stand (2022). Of course, various other alternative configurations for retainers (2030) can be used as will be apparent to those of ordinary skill in the art in view of the teachings herein.

In an exemplary use, device holder (2010) is used substantially the same as device holder (1010) described above. For instance, probe protector (1030) can be initially secured to probe (100). Once secured thereto, the distal end (1036) probe protector (1030) can be first inserted into opening (2021) of mount (2020). Once positioned therein, probe protector (1030) can be pivoted to position flange (1038) within well (2048) of stand (2022). As described above, positioning flange (1038) within well (2048) results in longitudinal fastening of probe protector (1030) to permit removal of probe (100) from probe protector (1030) for a biopsy procedure. Upon completion of the biopsy procedure, probe protector (1030) can then be removed from device holder (2010) by reversing the insertion procedure described above.

Unlike the use described above with respect to device holder (1010), it should be understood that the present use may require at least some more precise manipulation of probe protector (1030). For instance, as described above, device holder (2010) of the present example includes retainers (2030). Thus, in the presence of retainers (2030), probe protector (1030) may require at least some more specific manipulation depending on the structure of retainers (2030).

To manipulate probe protector (1030) into retainers (2030), probe protector (1030) is first pivoted to align with lateral opening (2034) defined by each overhang (2032). Once probe protector (1030) is aligned, probe protector (1030) can be pivoted laterally into the space beneath each overhang (2032). Once beneath each overhang (2032), probe protector (1030) can be pivoted downwardly to position flange (1038) into well (2048). At this stage, probe protector (1030) is longitudinally locked for removal of probe (100) and the performance of a biopsy procedure. Once the biopsy procedure is complete, probe protector (1030) can be removed by reversing the insertion procedure described above.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A device holder, comprising: (a) a needle holder, wherein the needle holder includes an elongated housing extending between an open receiver and a closed tip, wherein the open receiver is configured to releasably receive a biopsy device within the elongated housing, wherein the closed tip is configured to fluidly isolate at least a portion of the biopsy device when received within the elongated housing, wherein the elongated housing includes a pair of latches; (b) a mount holder, wherein the mount holder includes an inner channel extending between a proximal opening and a distal opening, wherein the mount holder further includes an engagement mechanism adjacent to the proximal opening; wherein the elongated housing has a longitudinal length greater than a channel length of the inner channel; wherein the mount holder is configured to removably receive the needle holder at the proximal opening such that the elongated housing extends through the distal opening; and wherein the engagement mechanism is configured to releasably engage the pair of latches as the needle holder is slidably received within the mount holder.

EXAMPLE 2

The device holder of Example 1, wherein the engagement mechanism includes an inner shelf and an inner sidewall, wherein the inner shelf is positioned along the perimeter of the proximal opening, wherein the inner sidewall is positioned along the channel length of the inner channel, wherein the inner shelf and inner sidewall extend laterally from an interior surface of the inner channel and into the inner channel.

EXAMPLE 3

The device holder of Example 2, wherein the inner shelf and inner sidewall are configured to inhibit the proximal movement of the pair of latches.

EXAMPLE 4

The device holder of Example 3, wherein the mount holder further includes a pair of ramps, wherein the pair of ramps have a tapered surface extending from the interior surface of the inner channel to the proximal opening, wherein the pair of ramps are configured to allow for the proximal movement of the pair of latches towards the proximal opening and out from the inner channel.

EXAMPLE 5

The device holder of Example 1, wherein the mount holder is fixedly attached to a control module cart, wherein the mount holder extends from the control module cart to a suspended position such that the mount holder contacts the control module cart at a single isolated point.

EXAMPLE 6

The device holder of any one or more of Examples 1 through 6, further including a holster holder configured to receive a disengaged-portion of the biopsy device.

EXAMPLE 7

The device holder of Example 5, wherein the holster holder is integrally formed with the mount holder.

EXAMPLE 8

The device holder of Example 1, wherein the needle holder further includes a pair of notches along the elongated housing, wherein the pair of notches are proximal to the open receiver.

EXAMPLE 9

The device holder of Example 8, wherein the pair of notches are configured to engage a corresponding latch of the biopsy device to releasably attach the needle holder to the biopsy device.

EXAMPLE 10

The device holder of Example 1, wherein the mount holder further includes a chamfered edge along the proximal opening, wherein the chamfered edge is configured to forcibly deform the pair of latches inwardly as the needle holder is slidably received by the mount holder.

EXAMPLE 11

The device holder of Example 1, wherein the pair of latches are spring tabs configured to deform inwardly into the elongated housing as the needle holder is received by the proximal opening of the mount holder.

EXAMPLE 12

The device holder of Example 11, wherein the pair of latches are configured to deform outwardly from the elongated housing as the pair of latches are received within the inner channel of the mount holder.

EXAMPLE 13

The device holder of Example 1, wherein the needle holder further includes a pair of locking tabs along the elongated housing, wherein the pair of locking tabs are proximal to the pair of latches.

EXAMPLE 14

The device holder of Example 13, wherein the pair of locking tabs are protrusions extending laterally from the elongated housing.

EXAMPLE 15

The device holder of Example 14, wherein the pair of locking tabs are configured to prevent the needle holder from slidably translating into the inner channel of the mount holder.

EXAMPLE 16

A device holder, comprising: (a) a needle holder, wherein the needle holder includes an elongated housing extending between an open receiver and a closed tip, wherein the open receiver is configured to releasably receive a biopsy device within the elongated housing, wherein the closed tip is configured to fluidly isolate at least a portion of the biopsy device when received within the elongated housing, wherein the elongated housing includes a pair of notches configured to selectively couple the needle holder to the biopsy device; (b) a distal holder, wherein the distal holder includes an opening configured to pivotably receive the closed tip such that the needle holder is operable to pivot about the distal holder when the closed tip is received therein; and (c) a proximal holder, wherein the proximal holder includes an engagement mechanism configured to slidably receive the needle holder such that the elongated housing extends between the distal and proximal holders, wherein the engagement mechanism is configured to inhibit the proximal translation of the needle holder relative to the distal and proximal holders such that the engagement mechanism is configured to disengage the pair of notches of the needle holder from the biopsy device as the biopsy device is translated proximally.

EXAMPLE 17

The device holder of Example 16, wherein the distal and proximal holders are fixedly attached to a control module cart, wherein the distal and proximal holders extend from the control module cart to a suspended position such that the distal and proximal holders are positioned along an isolated surface from the control module cart.

EXAMPLE 18

The device holder of Example 16, further including a holster holder configured to receive a disengaged-portion of the biopsy device.

EXAMPLE 19

The device holder of Example 18, wherein the holster holder is integrally formed with at least a portion of the proximal holder or distal holder.

EXAMPLE 20

The device holder of Example 16, wherein the distal and proximal holders are configured to rotatably swivel relative to the control module cart.

EXAMPLE 21

The device holder of Example 16 through 20, further including a top plate and a bottom plate, wherein the top plate is positioned atop the bottom plate, wherein the top plate is configured to pivot relative to the bottom plate.

EXAMPLE 22

The device holder of Example 21, wherein the top plate includes a ball detent configured to engage the bottom plate.

EXAMPLE 23

The device holder of Example 21 through 22, wherein the bottom plate includes a track, wherein the track has at least two locking points configured to receive the ball detent therein.

EXAMPLE 24

The device holder of Example 21 through 23, wherein the ball detent is configured to snap into the at least two locking points to thereby fix the top plate at an orientation relative to the bottom plate.

EXAMPLE 25

The device holder of Example 16, wherein the needle holder includes a flange, wherein the flange is configured to engage the proximal holder.

EXAMPLE 26

The device holder of Example 25, wherein the proximal holder includes a receiver, wherein the receiver is sized and shaped to receive the flange such that the needle cover is removably engaged with the proximal holder when the flange is received within the receiver.

EXAMPLE 27

The device holder of any one or more of Examples 21 through 26, wherein the proximal holder includes one or more retainers, wherein each retainer of the one or more retainers is configured to block at least some pivoting movement of the needle holder relative to the proximal holder.

EXAMPLE 28

The device holder of any one or more of Examples 21 through 26, wherein the proximal holder includes one or more retainers, wherein each retainer of the one or more retainers includes an overhang, wherein the overhang extends over the engagement mechanism of the proximal holder such that the overhang is configured to block at least some pivoting movement of the needle holder relative to the proximal holder.

EXAMPLE 29

A device holder, comprising: (a) a probe protector, wherein the probe protector includes an elongated housing extending between a proximal opening and a closed tip, wherein the proximal opening is configured to releasably receive a biopsy device within the elongated housing, wherein the closed tip is configured to fluidly isolate at least a portion of the biopsy device when received within the elongated housing, wherein the elongated housing includes a pair of notches configured to selectively couple the probe protector to the biopsy device; (b) a mount, wherein the mount includes an opening configured to pivotably receive the closed tip such that the probe protector is operable to pivot about the mount when the closed tip is received therein; and (c) a stand, wherein the stand includes a channel and a well configured to slidably receive the probe protector such that the elongated housing extends between the mount and stand, wherein the well is configured to inhibit the proximal translation of the probe protector relative to the mount and stand such that the well is configured to disengage the pair of notches of the probe protector from the biopsy device as the biopsy device is translated proximally.

EXAMPLE 30

A system for mounting a biopsy device, comprising: (a) a cart, wherein the cart includes a working surface and a transportability feature, wherein the transportability feature is configured to allow the cart to selectively move; (b) a device holder, wherein the device holder is positioned along the working surface of the cart, wherein the device holder includes a holster holder, a mount, and a stand, wherein the mount includes an opening, wherein the stand includes a channel, wherein the mount is in parallel alignment with the stand such that the opening is aligned with the channel; (c) a probe protector, wherein the probe protector includes an elongated housing extending between a proximal opening and a distal tip; and (d) a biopsy device, wherein the biopsy device includes a holster, a probe, and a needle; wherein the probe protector is configured to receive the needle and a portion of the probe within the elongated housing; wherein the holster holder is configured to receive the holster; and wherein the mount and stand are mutually configured to releasably receive the probe protector with the needle and the probe of the biopsy device attached therein.

EXAMPLE 31

The system of Example 31, wherein the transportability feature is one or more wheels.

EXAMPLE 32

The system of Example 31, wherein the device holder extends from the working surface to a suspended position such that the biopsy device received by the mount and stand is physically isolated from contacting the cart.

EXAMPLE 33

The system of Example 31, wherein the probe protector further includes a pair of notches along the elongated housing, wherein the pair of notches are proximal to the proximal opening.

EXAMPLE 34

The system of Example 33, wherein the pair of notches are configured to engage a corresponding latch along the probe to releasably attach the probe protector to the biopsy device.

EXAMPLE 35

The system of Example 31, wherein the device holder is configured to rotatably swivel relative to the working surface of the cart.

EXAMPLE 36

The system of Example 35, further including a top plate and a bottom plate, wherein the top plate is positioned atop the bottom plate, wherein the top plate is configured to pivot relative to the bottom plate.

EXAMPLE 37

The system of Example 36, wherein the top plate includes a ball detent configured to engage the bottom plate.

EXAMPLE 38

The system of Example 36 through 37, wherein the bottom plate includes a track, wherein the track has one or more locking points2 configured to receive the ball detent therein.

EXAMPLE 39

The system of Example 37 through 38, wherein the ball detent is configured to snap into the one or more locking points to thereby fix the top plate at an orientation relative to the bottom plate.

EXAMPLE 40

The system of Example 31, wherein the probe protector further includes a flange, wherein the flange is configured to engage the stand.

EXAMPLE 41

The system of Example 40, wherein the stand includes a well, wherein the well is sized and shaped to receive the flange such that the probe protector is removably engaged with the stand when the flange is received within the well.

EXAMPLE 42

A method of mounting a biopsy device onto a control module cart with a single hand in a manner to preserve the sterility of the biopsy device, wherein the control module cart includes device holder including a mount, a stand and a holster holder, wherein the device holder is configured to pivot relative to the control module cart, the method comprising: (a) inserting a holster into the holster holder; (b) inserting an assembly of a probe protector and a biopsy device into the mount; (c) pivoting the assembly of the probe protector and the biopsy device relatively downward toward the control module cart until encountering the stand; (d) engaging a flange of the probe protector with a locking well of the stand such that the assembly of the probe protector and the biopsy device are translatably fixed relative to the mount and the stand; (e) removing the holster from the holster holder and installing the holster onto the biopsy device; (f) pivoting the device holder relative to the control module cart to thereby reposition the assembly of the probe protector and the biopsy device and the holster away from the control module cart; and (f) pulling the biopsy device proximally relative to the control module cart to thereby disengage the biopsy device from the probe protector such that the probe protector maintains fixed engagement with the mount and the stand.

EXAMPLE 43

The method of Example 40.42, further comprising inserting the biopsy device into the probe protector to thereby reassemble the assembly of the probe protector and the biopsy device such that the biopsy device resumes fixed engagement with the mount and the stand.

EXAMPLE 44

The method of Example 43, further comprising pivoting the assembly of the probe protector and the biopsy device relatively upward away from the control module cart thereby disengaging the flange of the probe protector from the locking well.

EXAMPLE 45

The method of Example 44, further comprising withdrawing the assembly of the probe protector and the biopsy device from inside the mount to thereby release the assembly from contact with the control module cart.

EXAMPLE 46

A method of mounting a biopsy device onto a control module cart with a single hand, the method comprising: (a) inserting a holster into a holster holder, wherein the holster holder is secured to a device holder that is mounted to a portion of the control module cart; (b) inserting at least a portion of a probe protector into a mount, wherein the mount is secured to the device holder that is mounted to a portion of the control module cart; (c) pivoting a proximal end of the probe protector toward the control module cart until encountering a stand; (d) engaging a flange of the probe protector with a locking well of the stand such that the probe protector is translatably fixed relative to the mount and the stand; (e) removing the holster from the holster holder and installing the holster onto a portion of a probe.

EXAMPLE 47

The method of Example 46, further comprising pivoting the device holder relative to the control module cart to thereby reposition the probe protector relative to the control module cart.

EXAMPLE 48

The method of any one or more of Examples 46 through 47, pulling the probe proximally relative to the control module cart to thereby disengage the probe from the probe protector such that the probe protector maintains fixed engagement with the mount and the stand.

V. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A device holder, comprising:
   (a) a needle holder, wherein the needle holder includes an elongated housing extending between an open proximal end and a distal end and being adapted to releasably receive a portion of a biopsy device through the open proximal end, wherein the elongated housing includes a coupler configured to couple the needle holder to the biopsy device;
   (b) a distal holder, wherein the distal holder includes an opening configured to pivotably receive the distal end of the needle holder such that the needle holder is operable to pivot relative to the distal holder when the distal end of the needle holder is received therein; and
   (c) a proximal holder, wherein the proximal holder includes a longitudinal stop that engages with a portion of the needle holder to prevent the needle holder from proximal longitudinal movement such that the longitudinal stop is configured to disengage the coupler of the needle holder from the biopsy device when the biopsy device is moved proximally in a longitudinal direction.

2. The device holder of claim 1, the distal and proximal holders are fixedly attached to a control module cart, wherein the distal and proximal holders extend from the control module cart to a suspended position such that the distal and proximal holders are positioned along an isolated plane relative to the control module cart.

3. The device holder of claim 1, further comprising a holster holder configured to receive a disengaged portion of the biopsy device.

4. The device holder of claim 3, wherein the holster holder is integrally formed with at least a portion of the proximal holder or distal holder.

5. The device holder of claim 1, wherein the distal and proximal holders are configured to rotatably swivel relative to a control module cart.

6. The device holder of claim 1, further comprising a top plate and a bottom plate, wherein the top plate is positioned atop the bottom plate, wherein the top plate is configured to pivot relative to the bottom plate.

7. The device holder of claim 6, wherein the top plate includes a ball detent configured to engage the bottom plate.

8. The device holder of claim 6, wherein the bottom plate includes a track, wherein the track has at least two locking points configured to receive a ball detent therein.

9. The device holder of claim 6, wherein the top plate includes a ball detent configured to engage the bottom plate, wherein the bottom plate includes a track, wherein the track has at least two locking points configured to receive the ball detent therein, wherein the ball detent is configured to snap into the at least two locking points to thereby fix the top plate at an orientation relative to the bottom plate.

10. The device holder of claim 1, wherein the needle holder includes a flange, wherein the flange is configured to engage the proximal holder, wherein the proximal holder includes a receiver, wherein the receiver is sized and shaped to receive the flange such that the needle cover is removably engaged with the proximal holder when the flange is received within the receiver.

11. The device holder of claim 1, wherein the longitudinal stop is configured to permit lateral movement of the needle holder relative to the proximal holder to permit the needle holder to be removed together with a probe of the biopsy device.

12. The device holder of claim 1, wherein the proximal holder defines a channel, wherein the channel extends along an axis aligned with the opening of the distal holder.

13. The device holder of claim 1, wherein the proximal holder defines a channel, wherein the channel extends along an axis aligned with the opening of the distal holder, wherein the proximal holder further defines a well, wherein the well separates the channel into a proximal portion and a distal portion, wherein the well is configured to engage at least a portion of the needle holder.

14. The device holder of claim 1, wherein the proximal holder defines a channel, wherein the channel extends along an axis aligned with the opening of the distal holder, wherein the longitudinal stop of the proximal holder defines a well, wherein the well separates the channel into a proximal portion and a distal portion, wherein the needle holder includes a flange, wherein the well is configured to engage the flange of the needle holder.

15. The device holder of claim 1, wherein the proximal holder defines a channel, wherein the channel extends along an axis aligned with the opening of the distal holder, wherein the longitudinal stop of the proximal holder defines a rib, wherein the rib separates the channel into a proximal portion and a distal portion, wherein the needle holder includes a channel, wherein the needle holder is configured to pivot relative to the rib to pivot the channel into engagement with the rib.

16. A device holder for use holding a tip protector and a biopsy device, wherein the tip protector is adapted to releasably receive a needle of the biopsy device, the device holder comprising:
(a) a distal holder, wherein the distal holder includes an opening configured to pivotably receive a distal end of the tip protector such that the tip protector is operable to pivot relative to the distal holder when the distal end of the tip protector is received therein; and
(b) a proximal holder, wherein the proximal holder includes a longitudinal stop that engages with a portion of the tip protector to prevent the tip protector from proximal longitudinal movement such that the longitudinal stop is configured to disengage the tip protector from the biopsy device when the biopsy device is moved proximally in a longitudinal direction.

17. The device holder of claim 16, wherein the longitudinal stop of the proximal holder is defined by a v-shaped divot in a portion of the proximal holder.

18. The device holder of claim 16, wherein the distal holder and the proximal holder together define a holding axis, wherein the holding axis is oriented at an angle between 30° and 60°.

19. An apparatus for use holding a tip protector and a biopsy device, wherein the tip protector is adapted to releasably receive a needle of the biopsy device, the apparatus comprising:
(a) a mount having a receiver configured to pivotably receive a distal end of the tip protector such that the tip protector is operable to pivot relative to the mount when the distal end of the tip protector is received in the receiver; and
(b) a stand oriented proximally of the mount and including a well configured to engage a portion of the tip protector to prevent the tip protector from proximal longitudinal movement to thereby disengage the tip protector from the biopsy device when the biopsy device is moved proximally in a longitudinal direction.

20. The apparatus of claim 19, wherein the well is formed by a v-shaped cutout in a portion of the stand.

* * * * *